US006424343B1

United States Patent
Deering et al.

(10) Patent No.: US 6,424,343 B1
(45) Date of Patent: *Jul. 23, 2002

(54) GRAPHICS SYSTEM WITH PROGRAMMABLE REAL-TIME SAMPLE FILTERING

(75) Inventors: Michael F. Deering, Los Altos; David Naegle; Scott Nelson, both of Pleasanton, all of CA (US)

(73) Assignee: Sun Microsystems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/251,453

(22) Filed: Feb. 17, 1999

Related U.S. Application Data

(60) Provisional application No. 60/074,836, filed on Feb. 17, 1998.

(51) Int. Cl.[7] .............................................. G06T 15/00
(52) U.S. Cl. ........................................................ 345/419
(58) Field of Search ................................. 345/419, 420, 345/426, 428, 473, 427, 589, 611, 612, 613, 614, 615, 629

(56) References Cited

U.S. PATENT DOCUMENTS

| 5,117,289 A | | 5/1992 | Farley et al. ............... 358/443 |
| 5,287,438 A | * | 2/1994 | Kelleher .................. 394/132 |
| 5,446,834 A | | 8/1995 | Deering ..................... 345/427 |

(List continued on next page.)

FOREIGN PATENT DOCUMENTS

| EP | 0 463 700 | 1/1992 |
| EP | 0 506 429 | 9/1992 |
| GB | 0 278 524 | 11/1994 |
| WO | 91/14995 | 10/1991 |

OTHER PUBLICATIONS

Bjernfald, "The Memory System Makes The Difference," © 1999 Evans & Sutherland Computer Corporation, pp. 1–11.
Patent Abstract of Japan, vol. 98,No. 007, Mar. 31, 1998 and JP 08 063608 A.
"Simulating Peripheral Vision in Immersive Virtual Environments,"M. Slater, et al., Nov. 1993, No. 6, Headington hill Hall, Oxford, Gb, pp. 80–82, 91–94, and 105.
The RenderMan Companion, "A Programmer's Guide to Realistic Computer Graphics," Steve Upstill, 1990, pp. 137–146, 171–178, 193–237, and 273–309.
"Principles of Digital Image Synthesis," Andrew S. Glassner, vol. 1, Morgan Kaufman Publisher's, Inc., San Francisco, CA., 1995, pp. 243–244, 359–365.
"CIG Scene Realism: The World Tomorrow," Cosman, et al., Evans & Sutherland Computer Corporation Salt Lake City, UT, Jan. 29, 1999, p.18 pages.

(List continued on next page.)

*Primary Examiner*—Mark Zimmerman
*Assistant Examiner*—Enrique L Santiago
(74) *Attorney, Agent, or Firm*—Conley, Rose & Tayon

(57) ABSTRACT

A method and computer graphics system capable of supersampling and performing programmable real-time filtering or convolution are disclosed. In one embodiment, the computer graphics system may comprise a graphics processor, a sample buffer, and a sample-to-pixel calculation unit. The graphics processor may be configured to generate a plurality of samples. The sample buffer, which is coupled to the graphics processor, is configured to store the samples and may be configured to double-buffer at least part of the stored samples. The sample-to-pixel calculation unit is programmable to select a variable number of stored samples from the sample buffer to filter into an output pixel. The sample-to-pixel calculation unit performs the filter process in real-time, and may be programmable to use a number of different filter types in.a single frame. The sample buffer may be supersampled, and the samples may be positioned according to a regular grid, a perturbed regular grid, or a stochastic grid.

74 Claims, 22 Drawing Sheets

U.S. PATENT DOCUMENTS

| | | | | |
|---|---|---|---|---|
| 5,481,669 A | * | 1/1996 | Poulton et al. | 345/505 |
| 5,594,854 A | | 1/1997 | Baldwin et al. | 345/441 |
| 5,619,438 A | | 4/1997 | Farley et al. | 708/313 |
| 5,638,176 A | | 6/1997 | Hobbs et al. | 356/355 |
| 5,668,940 A | * | 9/1997 | Steiner et al. | 345/429 |
| 5,742,277 A | * | 4/1998 | Gossett et al. | 345/611 |
| 5,757,375 A | * | 5/1998 | Kawase | 345/429 |
| 5,774,110 A | * | 6/1998 | Edelson | 345/131 |
| 5,793,371 A | | 8/1998 | Deering | 345/418 |
| 5,999,187 A | * | 12/1999 | Dehmlow et al. | 345/420 |
| 6,072,498 A | * | 6/2000 | Brittain et al. | 345/428 |
| 6,072,500 A | * | 6/2000 | Foran et al. | 345/431 |
| 6,204,859 B1 | * | 3/2001 | Jouppi et al. | 345/422 |
| 6,313,838 B1 | * | 11/2001 | Deering | 345/420 |

OTHER PUBLICATIONS

Computer Graphics, "Principles and Practice," Second Edition In C, Foley,. et al., Addison–Wesley Publishing Co., 1996, pp. 620, 643–645, 778–791.

"Spatial Vision," De Valois, et al., Oxford Psychology Series No. 14, 1990, pp. 38–60.

International Search Report, Jan. 6, 1999, PCT/US 99/03270.

* cited by examiner

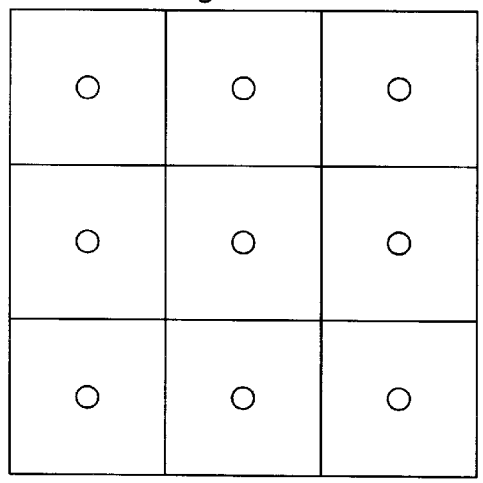
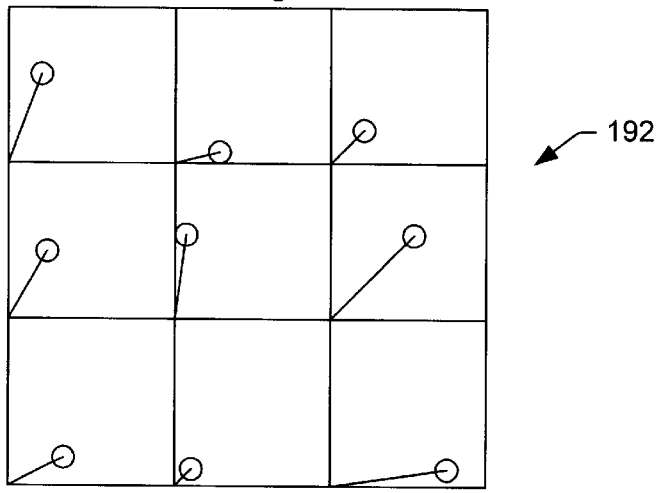
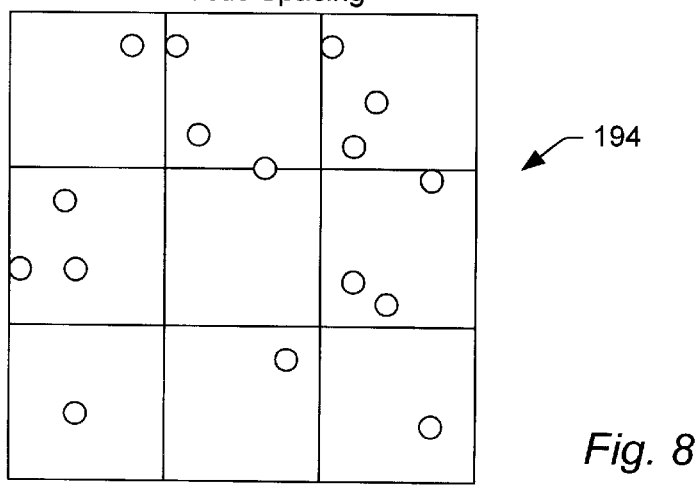
Fig. 8

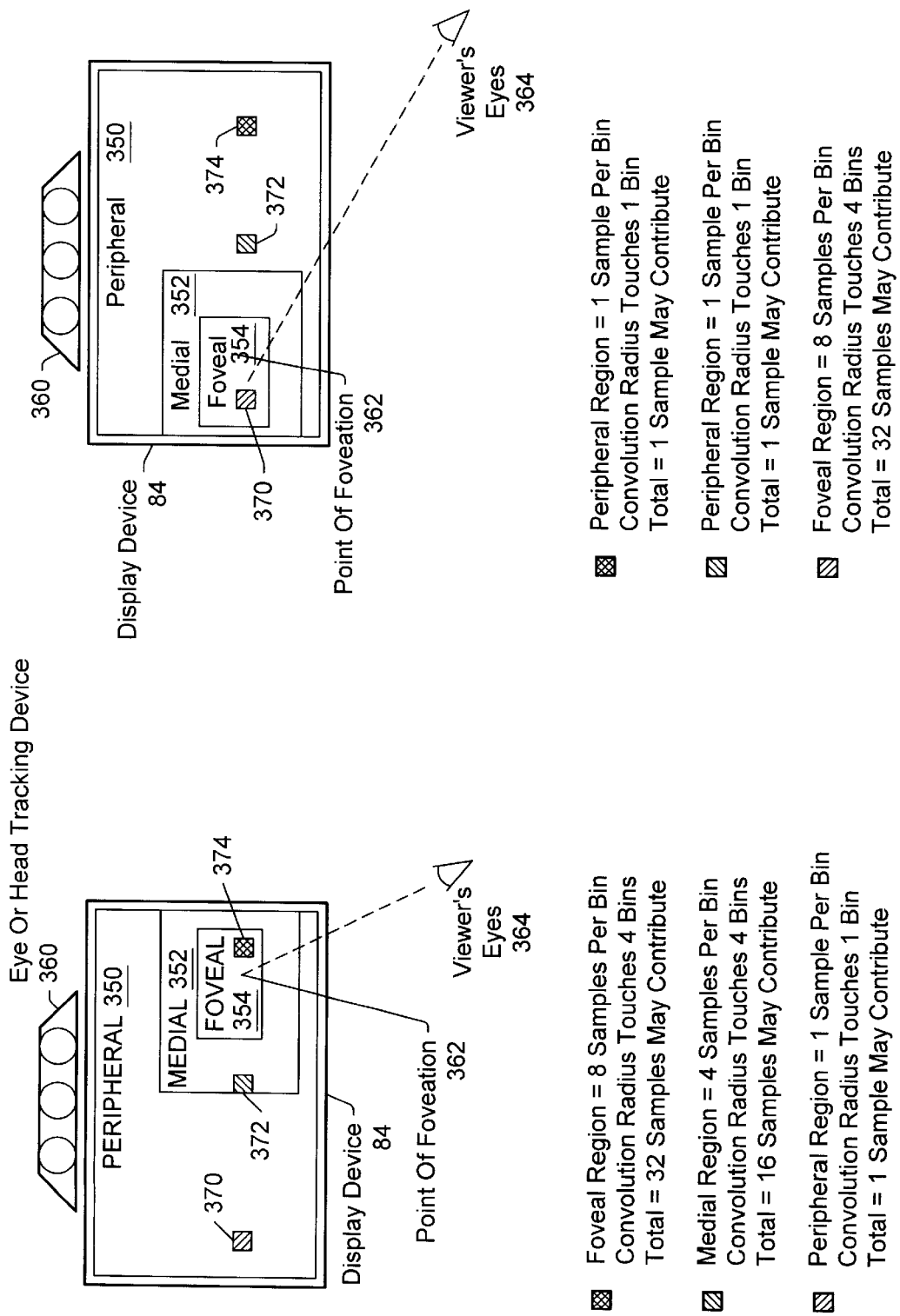

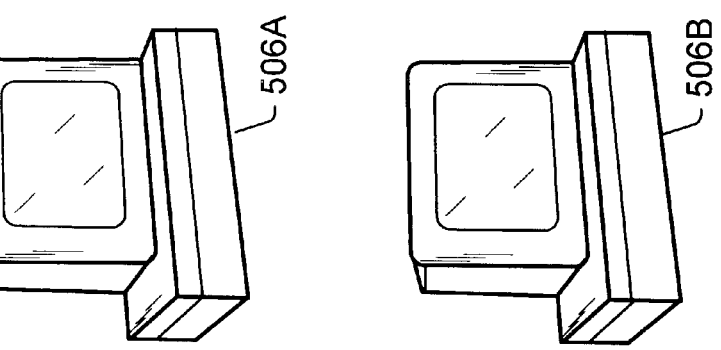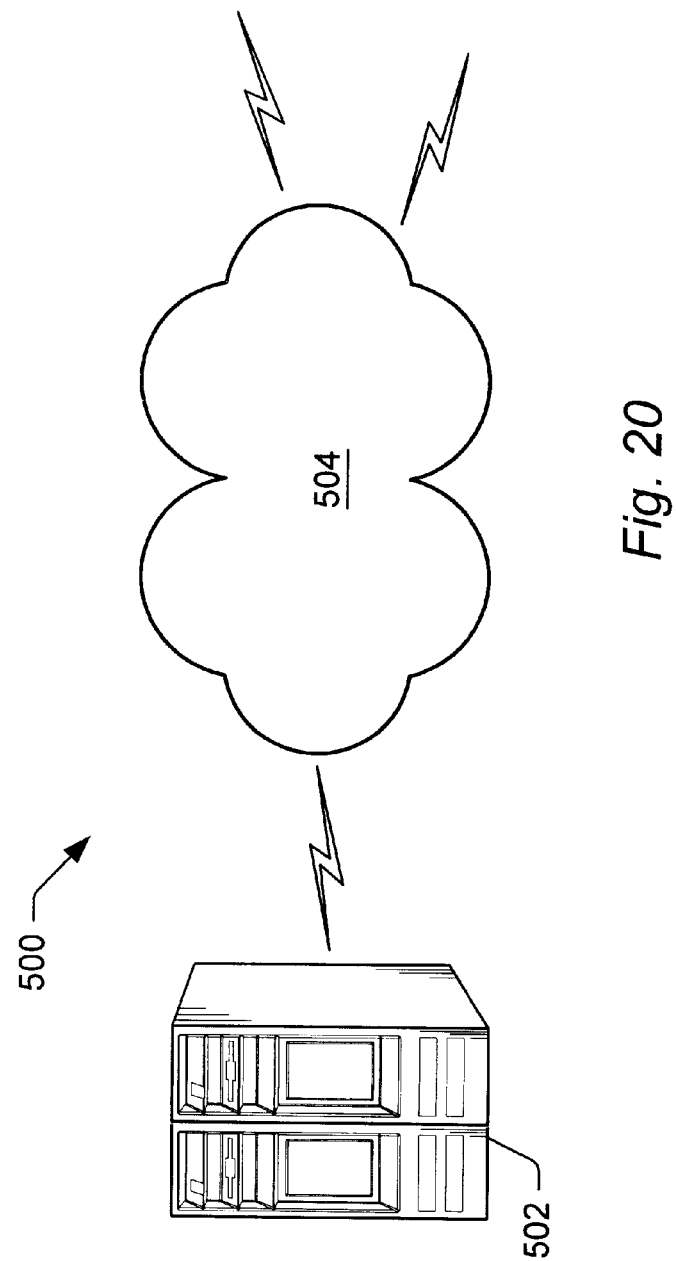
Fig. 20

GRAPHICS SYSTEM WITH PROGRAMMABLE REAL-TIME SAMPLE FILTERING

This application claims the benefit of U.S. provisional application No. 60/074,836, filed Feb. 17, 1998.

BACKGROUND OF THE INVENTION

1. Field of the Invention

This invention relates generally to the field of computer graphics and, more particularly, to high performance graphics systems.

2. Description of the Related Art

A computer system typically relies upon its graphics system for producing visual output on the computer screen or display device. Early graphics systems were only responsible for taking what the processor produced as output and displaying it on the screen. In essence, they acted as simple translators or interfaces. Modern graphics systems, however, incorporate graphics processors with a great deal of processing power. They now act more like coprocessors rather than simple translators. This change is due to the recent increase in both the complexity and amount of data being sent to the display device. For example, modem computer displays have many more pixels, greater color depth, and are able to display more complex images with higher refresh rates than earlier models. Similarly, the images displayed are now more complex and may involve advanced techniques such as anti-aliasing and texture mapping.

As a result, without considerable processing power in the graphics system, the CPU would spend a great deal of time performing graphics calculations. This could rob the computer system of the processing power needed for performing other tasks associated with program execution and thereby dramatically reduce overall system performance. With a powerful graphics system, however, when the CPU is instructed to draw a box on the screen, the CPU is freed from having to compute the position and color of each pixel. Instead, the CPU may send a request to the video card stating "draw a box at these coordinates." The graphics system then draws the box, freeing the processor to perform other tasks.

Generally, a graphics system in a computer (also referred to as a graphics system) is a type of video adapter that contains its own processor to boost performance levels. These processors are specialized for computing graphical transformations, so they tend to achieve better results than the general-purpose CPU used by the computer system. In addition, they free up the computer's CPU to execute other commands while the graphics system is handling graphics computations. The popularity of graphical applications, and especially multimedia applications, has made high performance graphics systems a common feature of computer systems. Most computer manufacturers now bundle a high performance graphics system with their systems.

Since graphics systems typically perform only a limited set of functions, they may be customized and therefore far more efficient at graphics operations than the computer's general-purpose central processor. While early graphics systems were limited to performing two-dimensional (2D) graphics, their functionality has increased to support three-dimensional (3D) wire-frame graphics, 3D solids, and now includes support for three-dimensional (3D) graphics with textures and special effects such as advanced shading, fogging, alpha-blending, and specular highlighting.

The processing power of 3D graphics systems has been improving at a breakneck pace. A few years ago, shaded images of simple objects could only be rendered at a few frames per second, while today's systems support rendering of complex objects at 60 Hz or higher. At this rate of increase, in the not too distant future, graphics systems will literally be able to render more pixels than a single human's visual system can perceive.

While this extra performance may be useable in multiple-viewer environments, it may be wasted in more common primarily single-viewer environments. Thus, a graphics system is desired which is capable of matching the variable nature of the human resolution system (i.e., capable of putting the quality where it is needed or most perceivable).

While the number of pixels is an important factor in determining graphics system performance, another factor of equal import is the quality of the image. For example, an image with a high pixel density may still appear unrealistic if edges within the image are too sharp or jagged (also referred to as "aliased"). One well-known technique to overcome these problems is anti-aliasing. Anti-aliasing involves smoothing the edges of objects by shading pixels along the borders of graphical elements. More specifically, anti-aliasing entails removing higher frequency components from an image before they cause disturbing visual artifacts. For example, anti-aliasing may soften or smooth high contrast edges in an image by forcing certain pixels to intermediate values (e.g., around the silhouette of a bright object superimposed against a dark background).

Another visual effect used to increase the realism of computer images is alpha blending. Alpha blending is a technique that controls the transparency of an object, allowing realistic rendering of translucent surfaces such as water or glass. Another effect used to improve realism is fogging. Fogging obscures an object as it moves away from the viewer. Simple fogging is a special case of alpha blending in which the degree of alpha changes with distance so that the object appears to vanish into a haze as the object moves away from the viewer. This simple fogging may also be referred to as "depth cueing" or atmospheric attenuation, i.e., lowering the contrast of an object so that it appears less prominent as it recedes. More complex types of fogging go beyond a simple linear function to provide more complex relationships between the level of translucence and an object's distance from the viewer. Current state of the art software systems go even further by utilizing atmospheric models to provide low-lying fog with improved realism.

While the techniques listed above may dramatically improve the appearance of computer graphics images, they also have certain limitations. In particular, they may introduce their own aberrations and are typically limited by the density of pixels displayed on the display device.

As a result, a graphics system is desired which is capable of utilizing increased performance levels to increase not only the number of pixels rendered but also the quality of the image rendered. In addition, a graphics system is desired which is capable of utilizing increases in processing power to improve the results of graphics effects such as anti-aliasing.

Prior art graphics systems have generally fallen short of these goals. Prior art graphics systems use a conventional frame buffer for refreshing pixel/video data on the display. The frame buffer stores rows and columns of pixels; that exactly correspond to respective row and column locations on the display. Prior art graphics system render 2D and/or 3D images or objects into the frame buffer in pixel form, and then read the pixels from the frame buffer during a screen refresh to refresh the display. Thus, the frame buffer stores the output pixels that are provided to the display. To reduce visual artifacts that may be created by refreshing the screen at the same time the frame buffer is being updated, most graphics systems' frame buffers are double-buffered.

To obtain more realistic images, some prior art graphics systems have gone further by generating more than one sample per pixel. As used herein, the term "sample" refers to calculated color information that indicates the color, depth (z), transparency, and potentially other information, of a particular point on an object or image. For example a sample may comprise the following component values: a red value, a green value, a blue value, a z value, and an alpha value (e.g., representing the transparency of the sample). A sample may also comprise other information, e.g., a z-depth value, a blur value, an intensity value, brighter-than-bright information, and an indicator that the sample consists partially or completely of control information rather than color information (i.e., "sample control information"). By calculating more samples than pixels (i.e., super-sampling), a more detailed image is calculated than can be displayed on the display device. For example, a graphics system may calculate four samples for each pixel to be output to the display device. After the samples are calculated, they are then combined or filtered to form the pixels that are stored in the frame buffer and then conveyed to the display device. Using pixels formed in this manner may create a more realistic final image because overly abrupt changes in the image may be smoothed by the filtering process.

These prior art super-sampling systems typically generate a number of samples that are far greater than the number of pixel locations on the display. These prior art systems typically have rendering processors that calculate the samples and store them into a render buffer. Filtering hardware then reads the samples from the render buffer, filters the samples to create pixels, and then stores the pixels in a traditional frame buffer. The traditional frame buffer is typically double-buffered, with one side being used for refreshing the display device while the other side is updated by the filtering hardware. Once the samples have been filtered, the resulting pixels are stored in a traditional frame buffer that is used to refresh to display device. These systems, however, have generally suffered from limitations imposed by the conventional frame buffer and by the added latency caused by the render buffer and filtering. Therefore, an improved graphics system is desired which includes the benefits of pixel super-sampling while avoiding the drawbacks of the conventional frame buffer.

SUMMARY OF THE INVENTION

The present invention comprises a computer graphics system that utilizes a super-sampled sample buffer and a programmable sample-to-pixel calculation unit for refreshing the display. In one embodiment, the graphics system may have a graphics processor, a super-sampled sample buffer, and a sample-to-pixel calculation unit.

The graphics processor generates a plurality of samples and stores them into a sample buffer. The graphics processor preferably generates and stores more than one sample for at least a subset of the pixel locations on the display. Thus, the sample buffer is a super-sampled sample buffer which stores a number of samples that, in some embodiments, may be far greater than the number of pixel locations on the display. In other embodiments, the total number of samples may be closer to, equal to, or even less than the total number of pixel locations on the display device, but the samples may be more densely positioned in certain areas and less densely positioned in other areas.

The sample-to-pixel calculation unit is configured to read the samples from the super-sampled sample buffer and filter or convolve the samples into respective output pixels, wherein the output pixels are then provided to refresh the display. Note as used herein the terms "filter" and "convolve" are used interchangeably and refer to mathematically manipulating one or more samples to generate a pixel (e.g., by averaging, by applying a convolution function, by summing, by applying a filtering function, by weighting the samples and then manipulating them, by applying a randomized function, etc.). The sample-to-pixel calculation unit selects one or more samples and filters them to generate an output pixel. Note the number of samples selected and or filtered by the sample-to-pixel calculation unit may be one or, in the preferred embodiment, greater than one.

In some embodiments, the number of samples used to form each pixel may vary. For example, the underlying average sample density in the sample buffer may vary, the extent of the filter may vary, or the number of samples for a particular pixel may vary due to stochastic variations in the sample density. In some embodiments the number may vary on a per-pixel basis, on a per-scan line basis, on a per-region basis, on a per-frame basis, or the number may remain constant. The sample-to-pixel calculation unit may access the samples from the super-sampled sample buffer, perform a real-time filtering operation, and then provide the resulting output pixels to the display in real-time. The graphics system may operate without a conventional frame buffer, i.e., the graphics system does not utilize a conventional frame buffer which stores the actual pixel values that are being refreshed on the display. Note some displays may have internal frame buffers, but these are considered an integral part of the display device, not the graphics system. Thus, the sample-to-pixel calculation units may calculate each pixel for each screen refresh on a real time basis. As used herein, the term "real-time" refers to a function that is performed at or near the display device's refresh rate." "On-the-fly" means at, near, or above the human visual system's perception capabilities for motion fusion (how often a picture must be changed to give the illusion of continuous motion) and flicker fusion (how often light intensity must be changed to give the illusion of continuous). These concepts are further described in the book "Spatial Vision" by Russel L. De Valois and Karen K. De Valois, Oxford University Press, 1988.

The sample-to-pixel calculation unit may be programmed to vary the number of samples used to generate respective output pixels. For example, the number of samples used may vary according to the location of the output pixel, e.g., the distance of the output pixel from a viewer's point of foveation. As used herein, the term "point of foveation" refers to a point (e.g., on a display screen) on which the center of a viewer's eyes' field of vision is focused. This point may move as the viewer's eyes move. For example, the point of foveation (which moves as the viewer's eyes move) may be located at the exact center of the display screen when the viewer is focussing on a small object displayed at the center of the screen.

The human visual system has varying levels of acuity, with the highest level of acuity occurring in the vicinity of the foveal pit of the retina. The foveal region receives light from the point of foveation and typically accounts for only a few degrees at the center of a human's of field of vision. Thus, to best match the human visual system, the graphics system may, in some embodiments, be configured to detect where the viewer's point of foveation is relative to the display device. This allows the graphics system to match the sample density to the human eye's acuity. Thus, more samples (and more processing power) will be allocated to areas of the display device that will be perceived by the highest acuity regions of the human visual system. Similarly, less samples and processing power will be devoted to regions that will be perceived by the lower acuity regions of the human visual system. Note however, it is not just the density of rods and cones in the eye that may be matched. Other factors also influence the perception of the human visual system, including the lens system, chromatic aberrations, and the neural pathways to the eye. For the purposes of matching computer displays to human retinal perception, the human brain's processing limits for visual input provides a useful target that future graphics systems may strive to match or exceed.

This type of graphics system may be implemented in a number of different ways. For example, eye-tracking sensors may be used to determine in what direction the viewer's eyes are directed. This may provide data with which to predict where the viewer's point of foveation is. Typically, head-mounted eye-tracking sensors may use an additional head-tracking sensor. Taken together, the eye- and head-tracking sensors can provide useful information about the position and movement of a viewer's point of foveation relative to the display device. Even further accuracy may be obtained using two eye-tracking sensors (i.e., one for each of the viewer's eyes). Thus two points of foveation may be detected for each viewer. Furthermore, in some configurations multiple viewers may each have their points of foveation detected. Other configurations may utilize a hand-tracking sensor (e.g., pointing wand or data glove) in combination with head- and or eye-tracking sensors. Another configuration may utilize a head-mounted display with various motion, direction, eye-tracking and or head-tracking sensors. A higher number of samples may be allocated to a region of a predetermined size centered at the calculated point of foveation to compensate for inaccuracies in the sensors (i.e., to ensure that the actual point of foveation will receive pixels generated from a high sample density). Note as used herein, the term "gaze tracking unit" refers to any combination of eye-tracking, head-tracking, hand tracking, and or body tracking sensors that provide information concerning one or more viewers points of foveation (there can be two points of foveation for each viewer). Examples of gaze tracking units may include one or more of the following: video cameras, "EMG" sensors that detect electrical currents in muscles, an eye-and-head tracker, an eye tracker, a head tracker, a hand tracker, a data glove, a wand, a data suit, a mouse, a body position sensor, a body position sensing chair, motion sensors, pressure sensors, acoustic sensors, and infra-red scanners/sensors. In other embodiments, the system may assume that the viewer's point of foveation is located at a fixed location near the center of the screen, or at a varying point of interest on the display created by the software application being executed.

Thus, the graphics system may be configured to utilize a greater number of samples in computing pixel values in areas where the viewers are able to perceive them, and a second lesser number of samples in computing pixel values in other areas where the viewers are not able to perceive them. The sample-to-pixel calculation unit, in varying the number of samples used, preferably varies the extent of the filter (e.g., the radius of the filter if a circularly symmetrical filter is used) used for generation of respective output pixels, which affects the number of samples used in calculating the output pixel (in addition, the rendering unit could have already varied the sample density). Alternatively, the sample-to-pixel calculation unit may select samples using other methods, e.g., randomly selecting/discarding samples to vary the number of samples during the filtering process.

The graphics processor may be similarly configured to vary the density of samples generated or rendered into the super-sampled sample buffer for different regions of the displayed image. These different sample density regions may be positioned based on the point of interest, cursor position, eye tracking, head tracking, etc. In other embodiments, the sample density may be varied on a scan line basis, a per-pixel basis, or a per-frame region basis.

In some embodiments, the graphics processor is further configurable to vary the positioning of the samples generated. For example, the samples may be positioned according to a regular grid, a perturbed regular gird, or a random distribution across the image. The sample positions may be stored in one or more sample position memories for fast access. In one embodiment, the sample positions may be stored as offsets, rather than absolute addresses or coordinates. In one embodiment, the graphics processor is operable to programmatically configure or vary the sample positions on a frame-by-frame basis or within a single frame.

A software program embodied on a computer medium and a method for operating a graphics subsystem are also contemplated. In one embodiment, the method comprises first calculating a plurality of sample locations, and then generating a sample for each sample pixel location. The samples may then be stored (e.g., into the super-sampled sample buffer). The sample locations may be specified according to any number of positioning or spacing schemes, e.g., a regular grid, a perturbed regular grid, or a stochastic grid. The stored samples may then be selected and filtered to form output pixels, which are provided in real time directly to the display without being stored in a traditional frame buffer. The samples may be selected according to their distance from the center of the convolution kernel (which corresponds to the estimated center of the output pixel). The selected samples may be multiplied by a weighting factor and summed. The output pixel is also normalized (e.g., through the use of pre-normalized weighting factors that are looked up, or by dividing the summed sample values by a calculated or pre-calculated normalization factor). In some embodiments, the selection process, weighting process, and normalization process are each programmable and changeable within each particular frame on a real-time basis.

BRIEF DESCRIPTION OF THE DRAWINGS

The foregoing, as well as other objects, features, and advantages of this invention may be more completely understood by reference to the following detailed description when read together with the accompanying drawings in which:

FIG. 8 is a diagram illustrating details of three different embodiments of sample positioning schemes;

FIGS. 18A–B are diagrams illustrating one embodiment of a graphics system configured to utilize input from an eye tracking or head tracking device;

FIG. 20 is a diagram of one embodiment of a computer network connecting multiple computers.

Figure 1:
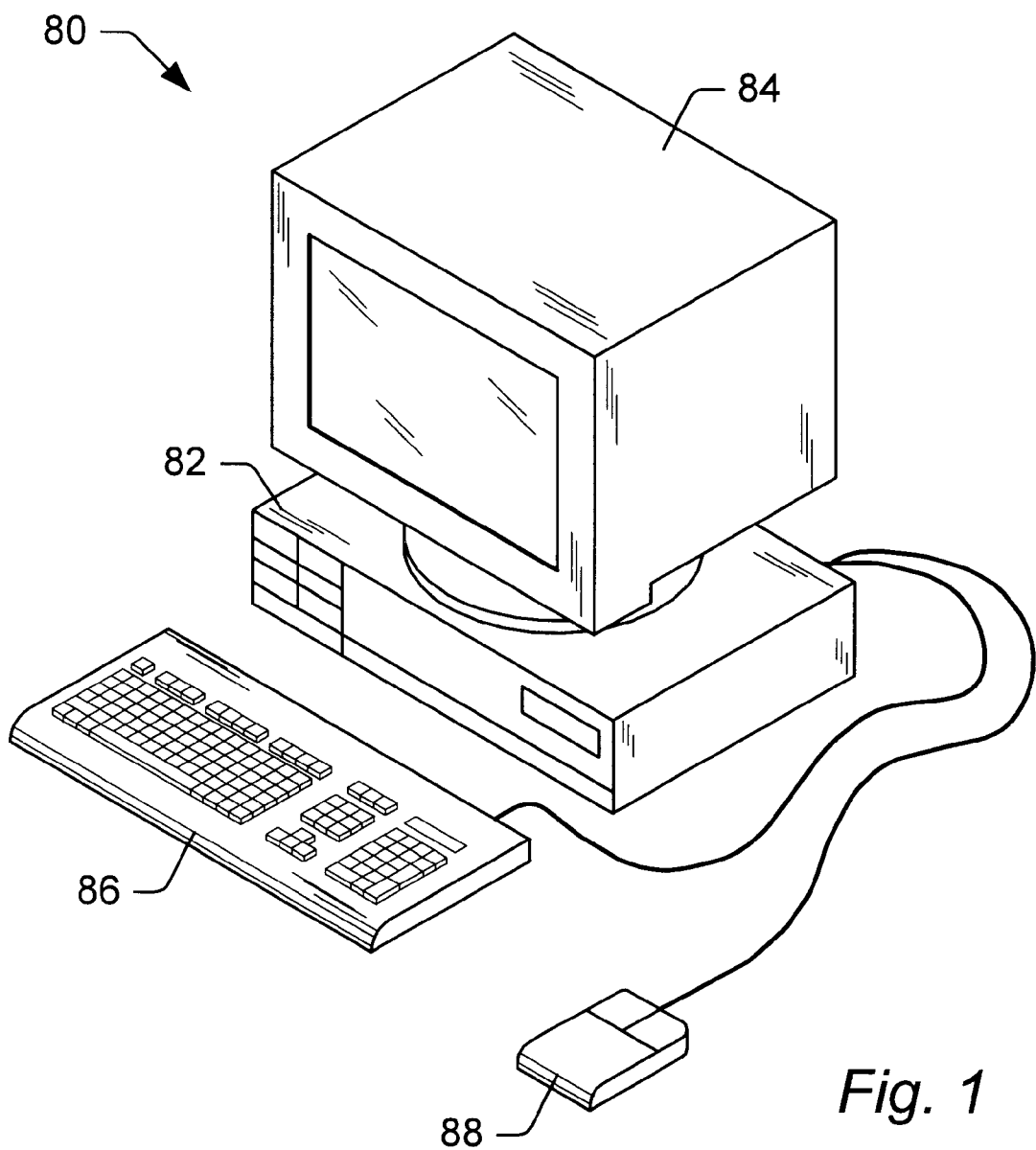
FIG. 1 illustrates one embodiment of a computer system that includes one embodiment of a graphics system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims.

DETAILED DESCRIPTION OF SEVERAL EMBODIMENTS

Computer System—FIG. 1

Referring now to FIG. 1, one embodiment of a computer system 80 that includes a three-dimensional (3-D) graphics system is shown. The 3-D graphics system may be comprised in any of various systems, including a computer system, network PC, Internet appliance, a television, including HDTV systems and interactive television systems, personal digital assistants (PDAs), and other devices which display 2D and or 3D graphics, among others.

As shown, the computer system 80 comprises a system unit 82 and a video monitor or display device 84 coupled to the system unit 82. The display device 84 may be any of various types of display monitors or devices (e.g., a CRT, LCD, or gas-plasma display). Various input devices may be connected to the computer system, including a keyboard 86 and/or a mouse 88, or other input device (e.g., a trackball, digitizer, tablet, six-degree of freedom input device, head tracker, eye tracker, data glove, body sensors, etc.). Application software may be executed by the computer system 80 to display 3-D graphical objects on display device 84. As described further below, the 3-D graphics system in computer system 80 includes a super-sampled sample buffer with a programmable real-time sample-to-pixel calculation unit to improve the quality and realism of images displayed on display device 84.

Figure 2:
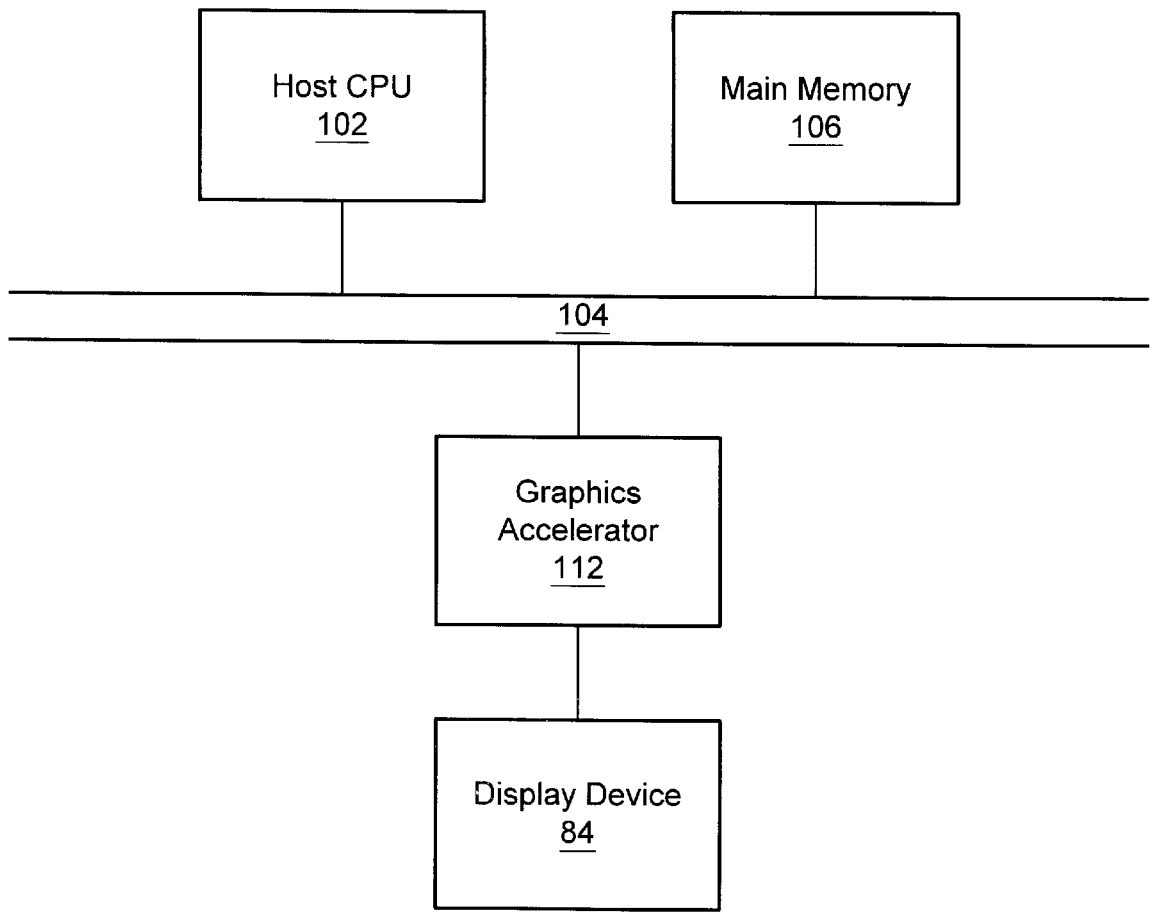
FIG. 2 is a simplified block diagram of the computer system of FIG. 1.

Computer System Block Diagram—FIG. 2

Referring now to FIG. 2, a simplified block diagram illustrating the computer system of FIG. 1 is shown. Elements of the computer system that are not necessary for an understanding of the present invention are not shown for convenience. As shown, the computer system 80 includes a central processing unit (CPU) 102 coupled to a high-speed memory bus or system bus 104 also referred to as the host bus 104. A system memory 106 may also be coupled to high-speed bus 104.

Host processor 102 may comprise one or more processors of varying types, e.g., microprocessors, multi-processors and CPUs. The system memory 106 may comprise any combination of different types of memory subsystems, including random access memories, (e.g., static random access memories or "SRAMs", synchronous dynamic random access memories or "SDRAMs", and Rambus dynamic access memories or "RDRAM", among others) and mass storage devices. The system bus or host bus 104 may comprise one or more communication or host computer buses (for communication between host processors, CPUs, and memory subsystems) as well as specialized subsystem buses.

A 3-D graphics system or graphics system 112 according to the present invention is coupled to the high-speed memory bus 104. The 3-D graphics system 112 may be coupled to the bus 104 by, for example, a crossbar switch or other bus connectivity logic. It is assumed that various other peripheral devices, or other buses, may be connected to the high-speed memory bus 104. It is noted that the 3-D graphics system may be coupled to one or more of the buses in computer system 80 and/or may be coupled to various types of buses. In addition, the 3D graphics system may be coupled to a communication port and thereby directly receive graphics data from an external source, e.g., the Internet or a network. As shown in the figure, display device 84 is connected to the 3-D graphics system 112 comprised in the computer system 80.

Host CPU 102 may transfer information to and from the graphics system 112 according to a programmed input/ output (I/O) protocol over host bus 104. Alternately, graphics system 112 may access the memory subsystem 106 according to a direct memory access (DMA) protocol or through intelligent bus mastering.

A graphics application program conforming to an application programming interface (API) such as OpenGL or Java 3D may execute on host CPU 102 and generate commands and data that define a geometric primitive (graphics data) such as a polygon for output on display device 84. As defined by the particular graphics interface used, these primitives may have separate color properties for the front and back surfaces. Host processor 102 may transfer these graphics data to memory subsystem 106. Thereafter, the host processor 102 may operate to transfer the graphics data to the graphics system 112 over the host bus 104. In another embodiment, the graphics system 112 may read in geometry data arrays over the host bus 104 using DMA access cycles. In yet another embodiment, the graphics system 112 may be coupled to the system memory 106 through a direct port, such as the Advanced Graphics Port (AGP) promulgated by Intel Corporation.

The graphics system may receive graphics data from any of various sources, including the host CPU 102 and/or the system memory 106, other memory, or from an external source such as a network, e.g., the Internet, or from a broadcast medium, e.g., television, or from other sources.

As will be described below, graphics system 112 may be configured to allow more efficient microcode control, which results in increased performance for handling of incoming color values corresponding to the polygons generated by host processor 102. Note while graphics system 112 is depicted as part of computer system 80, graphics system 112 may also be configured as a stand-alone device (e.g., with its own built-in display). Graphics system 112 may also be configured as a single chip device or as part of a system-on-a-chip or a multi-chip module.

Figure 3:
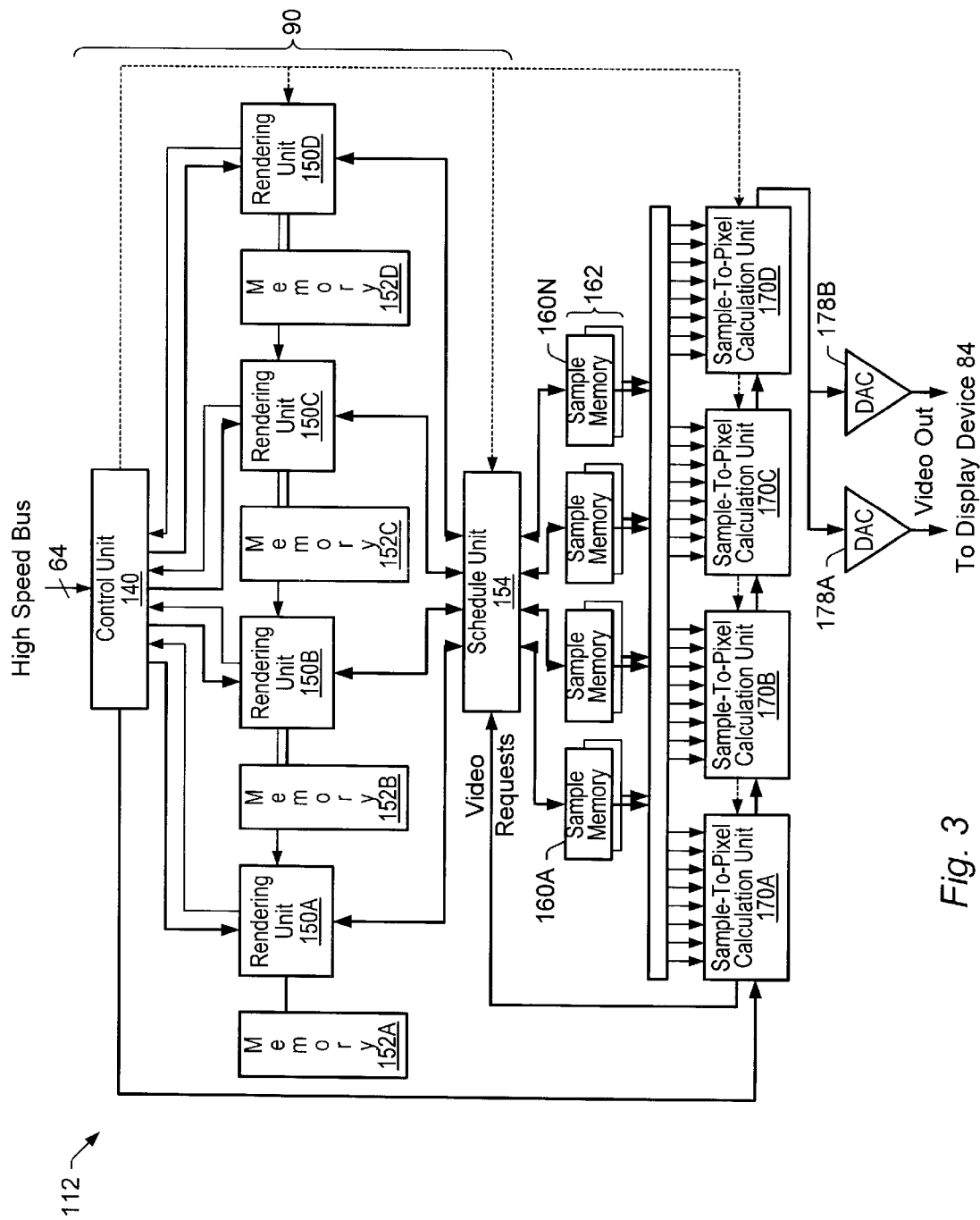
FIG. 3 is a block diagram illustrating more details of one embodiment of the graphics system of FIG. 1.

Graphics System—FIG. 3

Referring now to FIG. 3, a block diagram illustrating details of one embodiment of graphics system 112 is shown. As shown in the figure, graphics system 112 may comprise one or more graphics processors 90, one or more super-sampled sample buffers 162, and one or more sample-to-pixel calculation units 170A–D. Graphics system 112 may also comprise one or more digital-to-analog converters (DACs) 178A–B. Graphics processor 90 may be any suitable type of high performance processor (e.g., specialized graphics processors or calculation units, multimedia processors, DSPs, or general purpose processors). In one embodiment, graphics processor 90 may comprise one or more rendering units 150A–D. In the embodiment shown, however, graphics processor 90 also comprises one or more control units 140, one or more data memories 152A–D, and one or more schedule units 154. Sample buffer 162 may comprises one or more sample memories 160A–160N as shown in the figure.

A. Control Unit

Control unit 140 operates as the interface between graphics system 112 and computer system 80 by controlling the transfer of data between graphics system 112 and computer system 80. In embodiments of graphics system 112 that comprise two or more rendering units 150A–D, control unit 140 may also divide the stream of data received from computer system 80 into a corresponding number of parallel streams that are routed to the individual rendering units 150A–D. The graphics data may be received from computer system 80 in a compressed form. This may advantageously reduce the bandwidth requirements between computer system 80 and graphics system 112. In one embodiment, control unit 140 may be configured to split and route the data stream to rendering units 150A–D in compressed form.

The graphics data may comprise one or more graphics primitives. As used herein, the term graphics primitive includes polygons, parametric surfaces, splines, NURBS (non-uniform rational B-splines), sub-divisions surfaces, fractals, volume primitives, and particle systems. These graphics primitives are described in detail in the text book entitled "Computer Graphics: Principles and Practice" by James D. Foley, et al., published by Addison-Wesley Publishing Co., Inc., 1996. Note polygons are referred to throughout this detailed description for simplicity, but the embodiments and examples described may also be used with graphics data comprising other types of graphics primitives.

B. Rendering Units

Rendering units 150A–D (also referred to herein as draw units) are configured to receive graphics instructions and data from control unit 140 and then perform a number of functions, depending upon the exact implementation. For example, rendering units 150A–D may be configured to perform decompression (if the data is compressed), transformation, clipping, lighting, texturing, depth cueing, transparency processing, set-up, and screen space rendering of various graphics primitives occurring within the graphics data. Each of these features is described separately below.

Depending upon the type of compressed graphics data received, rendering units 150A–D may be configured to perform arithmetic decoding, run-length decoding, Huffman decoding, and dictionary decoding (e.g., LZ77, LZSS, LZ78, and LZW). In another embodiment, rendering units 150A–D may be configured to decode graphics data that has been compressed using geometric compression. Geometric compression of 3D graphics data may achieve significant reductions in data size while retaining most of the image quality. Two methods for compressing and decompressing 3D geometry are described in U.S. Pat. No. 5,793,371, application Ser. No. 08/511,294, (filed on Aug. 4, 1995, entitled "Method And Apparatus For Geometric Compression Of Three-Dimensional Graphics Data,") and U.S. patent application Ser. No. 09/095,777, filed on Jun. 11, 1998, entitled "Compression of Three-Dimensional Geometry Data Representing a Regularly Tiled Surface Portion of a Graphical Object,"). In embodiments of graphics system 112 that support decompression, the graphics data received by each rendering unit 150 is decompressed into one or more graphics "primitives" which may then be rendered. The term primitive refers to components of objects that define its shape (e.g., points, lines, triangles, polygons in two or three dimensions, polyhedra, or free-form surfaces in three dimensions). Rendering units 150 may be any suitable type of high performance processor (e.g., specialized graphics processors or calculation units, multimedia processors, DSPs, or general purpose processors).

Transformation refers to manipulating an object and includes translating the object (i.e., moving the object to a different location), scaling the object (i.e., stretching or shrinking), and rotating the object (e.g., in three-dimensional space, or "3-space").

Clipping refers to defining the limits of the displayed image (i.e., establishing a clipping region, usually a rectangle) and then not rendering or displaying pixels that fall outside those limits.

Lighting refers to calculating the illumination of the objects within the displayed image to determine what color and or brightness each individual object will have. Depending upon the shading algorithm being used (e.g., constant, Gourand, or Phong), lighting may be evaluated at a number of different locations. For example, if constant shading is used (i.e., each pixel of a polygon has the same lighting), then the lighting need only be calculated once per polygon. If Gourand shading is used, then the lighting is calculated once per vertex. Phong shading calculates the lighting on a per-pixel basis.

Set-up refers to mapping primitives to a three-dimensional viewport. This involves translating and transforming the objects from their original "world-coordinate" system to the established viewport's coordinates. This creates the correct perspective for three-dimensional objects displayed on the screen.

Screen-space rendering refers to the calculations performed to actually calculate the data used to generate each pixel that will be displayed. In prior art systems, each pixel is calculated and then stored in a frame buffer. The contents of the frame buffer are then output to the display device to create the final image. In the embodiment of graphics system 112 shown in the figure, however, rendering units 150A–D calculate "samples" instead of actual pixel data. This allows rendering units 150A–D to "super-sample" or calculate more than one sample per pixel. Super-sampling is described in greater detail below. Note that rendering units 150A–B may comprises a number of smaller functional units, e.g., a separate set-up/decompress unit and a lighting unit.

More details on super-sampling are discussed in the following books: "Principles of Digital Image Synthesis" by Andrew Glassner, 1995, Morgan Kaufman Publishing (Volume 1); and "Renderman Companion:" by Steve Upstill, 1990, Addison Wesley Publishing.

C. Data Memories

Each rendering unit 150A–D may be coupled to an instruction and data memory 152A–D. In one embodiment, each data memory 152A–D may be configured to store both data and instructions for rendering units 150A–D. While implementations may vary, in one embodiment each data memory 152A–D may comprise two 8 MByte SDRAMs providing a total of 16 MBytes of storage for each rendering unit 150A–D. In another embodiment, RDRAMs (Rambus DRAMs) may be used to support the decompression and set-up operations of each rendering unit, while SDRAMs may be used to support the draw functions of rendering units 150A–D.

D. Schedule Unit

Schedule unit 154 may be coupled between the rendering units 150A–D and the sample memories 160A–N. Schedule unit 154 is configured to sequence the completed samples and store them in sample memories 160A–N. Note in larger configurations, multiple schedule units 154 may be used in parallel. In one embodiment, schedule unit 154 may be implemented as a crossbar switch.

E. Sample Memories

Super-sampled sample buffer 162 comprises sample memories 160A–160N, which are configured to store the plurality of samples generated by the rendering units. As used herein, the term "sample buffer" refers to one or more memories which store samples. As previously noted, one or more samples are filtered to form output pixels (i.e., pixels to be displayed on a display device). The number of samples stored may be greater than, equal to, or less than the total number of pixels output to the display device to refresh a single frame. Each sample may correspond to one or more output pixels. As used herein, a sample "corresponds" to an output pixel when the sample's information contributes to final output value of the pixel. Note, however, that some samples may contribute zero to their corresponding output pixel after filtering takes place.

Stated another way, the sample buffer stores a plurality of samples that have positions that correspond to locations in screen space on the display, i.e., the samples contribute to one or more output pixels on the display. The number of stored samples may be greater than the number of pixel locations, and more than one sample may be combined in the convolution (filtering) process to generate a particular output pixel displayed on the display device. Any given sample may contribute to one or more output pixels.

Sample memories 160A–160N may comprise any of a number of different types of memories (e.g., SDRAMs, SRAMs, RDRAMs, 3DRAMs, or next-generation 3DRAMs) in varying sizes. In one embodiment, each schedule unit 154 is coupled to four banks of sample memories, wherein each bank comprises four 3DRAM-64 memories. Together, the 3DRAM-64 memories may form a 116-bit deep super-sampled sample buffer that stores multiple samples per pixel. For example, in one embodiment, each sample memory 160A–160N may store up to sixteen samples per pixel.

3DRAM-64 memories are specialized memories configured to support full internal double buffering with single buffered Z in one chip. The double buffered portion comprises two RGBX buffers, wherein X is a fourth channel that can be used to store other information (e.g., alpha). 3DRAM-64 memories also have a lookup table that takes in window ID information and controls an internal 2-1 or 3-1 multiplexer that selects which buffer's contents will be output. 3DRAM-64 memories are next-generation 3DRAM memories that may soon be available from Mitsubishi Electric Corporation's Semiconductor Group. In one embodiment, four chips used in combination are sufficient to create a double-buffered 1280×1024 super-sampled sample buffer. Since the memories are internally double-buffered, the input pins for each of the two frame buffers in the double-buffered system are time multiplexed (using multiplexers within the memories). The output pins may similarly be time multiplexed. This allows reduced pin count while still providing the benefits of double buffering. 3DRAM-64 memories further reduce pin count by not having z output pins. Since z comparison and memory buffer selection is dealt with internally, this may simplify sample buffer 162 (e.g., using less or no selection logic on the output side). Use of 3DRAM-64 also reduces memory bandwidth since information may be written into the memory without the traditional process of reading data out, performing a z comparison, and then writing data back in. Instead, the data may be simply written into the 3DRAM-64, with the memory performing the steps described above internally.

However, in other embodiments of graphics system 112, other memories (e.g., SDRAMs, SRAMs, RDRAMs, or current generation 3DRAMs) may be used to form sample buffer 162.

Graphics processor 90 may be configured to generate a plurality of sample positions according to a particular sample positioning scheme (e.g., a regular grid, a perturbed regular grid, etc.). Alternatively, the sample positions (or offsets that are added to regular grid positions to form the sample positions) may be read from a sample position memory (e.g., a RAM/ROM table). Upon receiving a polygon that is to be rendered, graphics processor 90 determines which samples fall within the polygon based upon the sample positions. Graphics processor 90 renders the samples that fall within the polygon and stores rendered samples in sample memories 160A–N. Note as used herein the terms render and draw are used interchangeable and refer to calculating color values for samples. Depth values, alpha values, and other per-sample values may also be calculated in the rendering or drawing process.

E. Sample-to-pixel Calculation Units

Sample-to-pixel calculation units 170A–D may be coupled between sample memories 160A–N and DACs 178A–B. Sample-to-pixel calculation units 170A–D are configured to read selected samples from sample memories 160A–N and then perform a convolution (e.g., a filtering and weighting function or a low pass filter) on the samples to generate the output pixel values which are output to DACs 178A–B. The sample-to-pixel calculation units 170A–D may be programmable to allow them to perform different filter functions at different times, depending upon the type of output desired. In one embodiment, the sample-to-pixel calculation units 170A–D may implement a 5×5 super-sample reconstruction band-pass filter to convert the super-sampled sample buffer data (stored in sample memories 160A–N) to single pixel values. In other embodiments, calculation units 170A–D may filter a selected number of samples to calculate an output pixel. The filtered samples may be multiplied by a variable weighting factor that gives more or less weight to samples having positions close the center of the pixel being calculated. Other filtering functions may also be used either alone or in combination, e.g., tent filters, circular and elliptical filters, Mitchell filters, band pass filters, sync function filters, etc.

Sample-to-pixel calculation units 170A–D may also be configured with one or more of the following features: color look-up using pseudo color tables, direct color, inverse gamma correction, filtering of samples to pixels, and conversion of pixels to non-linear light space. Other features of sample-to-pixel calculation units 170A–D may include programmable video timing generators, programmable pixel clock synthesizers, and crossbar functions. Once the sample-to-pixel calculation units have manipulated the timing and color of each pixel, the pixels are output to DACs 178A–B.

F. DACs

DACs 178A–B operate as the final output stage of graphics system 112. The DACs 178A–B serve to translate the digital pixel data received from cross units 174A–B into analog video signals that are then sent to the display device. Note in one embodiment DACs 178A–B may be bypassed or omitted completely in order to output digital pixel data in lieu of analog video signals. This may be useful when display device 84 is based on a digital technology (e.g., an LCD-type display or a digital micro-mirror display).

Figure 4:
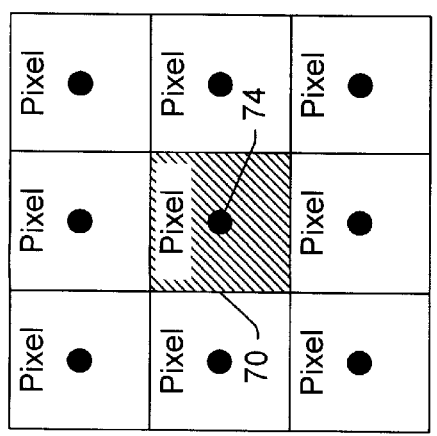
FIG. 4 is diagram illustrating traditional pixel calculation.

Super-Sampling—FIGS. 4–5

Turning now to FIG. 4, an example of traditional, non-super-sampled pixel value calculation is illustrated. Each pixel has exactly one data point calculated for it, and the single data point is located at the center of the pixel. For example, only one-data point (i.e., sample 74) contributes to value of pixel 70.

Figure 5B:
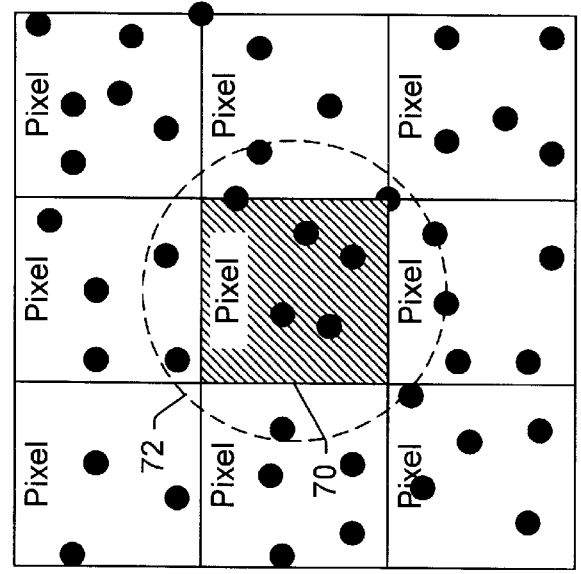
FIG. 5B is diagram illustrating a random distribution of samples.
Figure 5A:
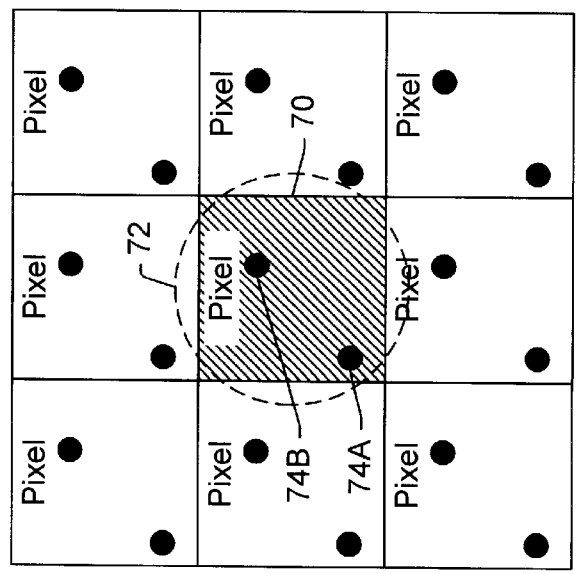
FIG. 5A is diagram illustrating one embodiment of super-sampling.

Turning now to FIG. 5A, an example of one embodiment of super-sampling is illustrated. In this embodiment, a number of samples are calculated. The number of samples may be related to the number of pixels or completely independent of the number of pixels. In this example, there are 18 samples distributed in a regular grid across nine pixels. Even with all the samples present in the figure, a simple one to one correlation could be made (e.g., by throwing out all but the sample nearest to the center of each pixel). However, the more interesting case is performing a filtering function on multiple samples to determine the final pixel values. Also, as noted above, a single sample can be used to generate a plurality of output pixels, i.e., sub-sampling.

A circular filter 72 is illustrated in the figure. In this example, samples 74A–B both contribute to the final value of pixel 70. This filtering process may advantageously improve the realism of the image displayed by smoothing abrupt edges in the displayed image (i.e., performing anti-aliasing). Filter 72 may simply average samples 74A–B to form the final value of output pixel 70, or it may increase the contribution of sample 74B (at the center of pixel 70) and diminish the contribution of sample 74A (i.e., the sample farther away from the center of pixel 70). Circular filter 72 is repositioned for each output pixel being calculated so the center of filter 72 coincides with the center position of the pixel being calculated. Other filters and filter positioning schemes are also possible and contemplated.

Turning now to FIG. 5B, another embodiment of super-sampling is illustrated. In this embodiment, however, the samples are positioned randomly. More specifically, different sample positions are selected and provided to graphics processor 90 (and render units 150A–D), which calculate color information to form samples at these different locations. Thus the number of samples falling within filter 72 may vary from pixel to pixel.

Super-Sampled Sample buffer with Real-Time Convolution—FIGS. 6–13

Figure 6:
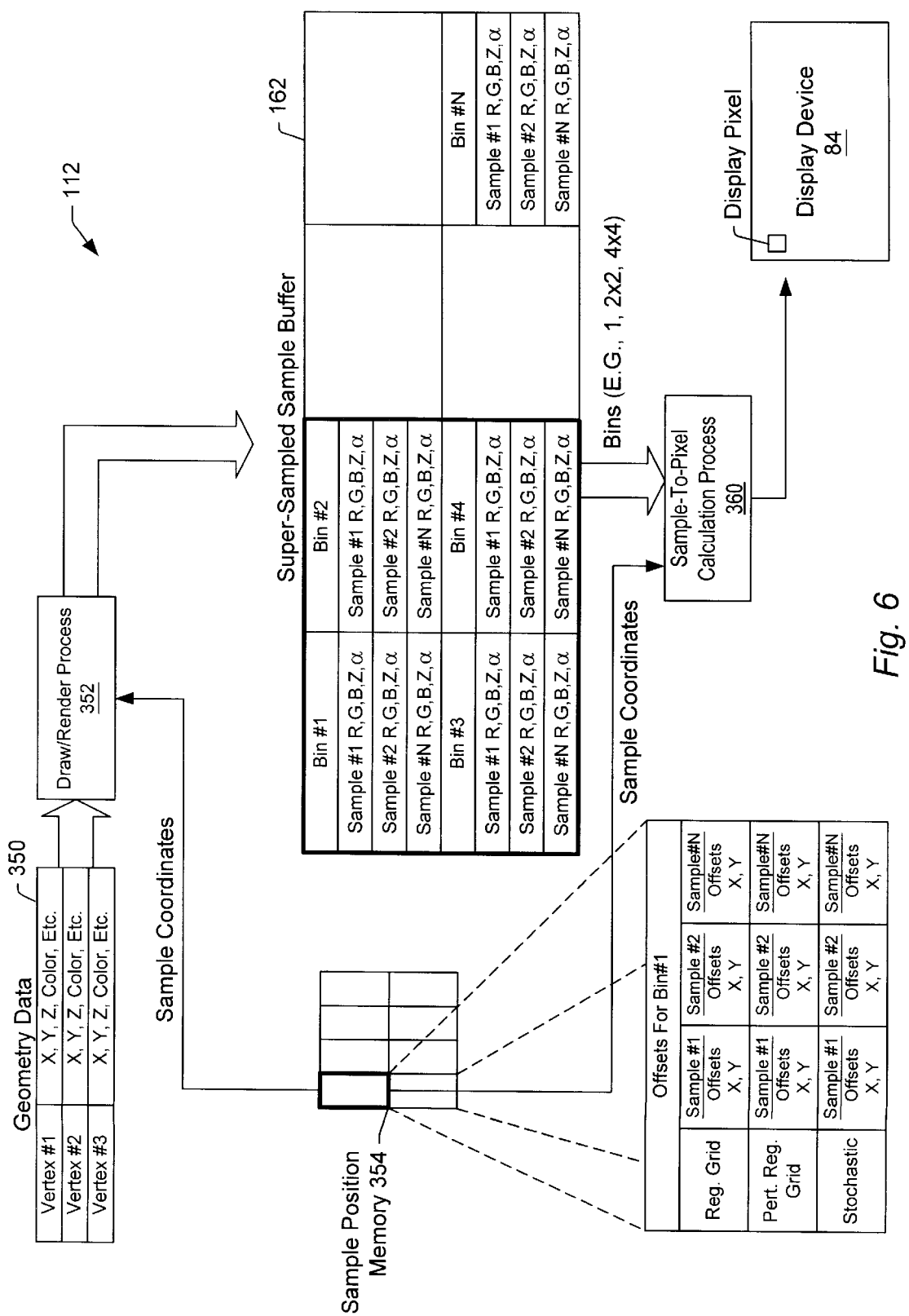
FIG. 6 is a diagram illustrating details of one embodiment of a graphics system having one embodiment of a variable resolution super-sampled sample buffer.

Turning now to FIG. 6, a diagram illustrating one possible configuration for the flow of data through one embodiment of graphics system 112 is shown. As the figure shows, geometry data 350 is received by graphics system 112 and used to perform draw process 352. The draw process 352 is implemented by one or more of control unit 140, rendering units 150, memories 152, and schedule unit 154. Geometry data 350 comprises data for one or more polygons. Each polygon comprises a plurality of vertices (e.g., three vertices in the case of a triangle), some of which may be shared. Data such as x, y, and z coordinates, color data, lighting data and texture map information may be included for each vertex.

In addition to the vertex data, draw process 352 (which may be performed by rendering units 150A–D) also receives sample coordinates from a sample position memory 354. In one embodiment, position memory 354 is embodied within rendering units 150A–D. In another embodiment, position memory 354 may be realized as part of texture and render memories 152A–152D, or as a separate memory. Sample position memory 354 is configured to store position information for samples that are calculated in draw process 352 and then stored into super-sampled sample buffer 162. In one embodiment, position memory 354 may be configured to store entire sample addresses. However, this may involve increasing the size of position memory 354. Alternatively, position memory 354 may be configured to store only x- and y-offsets for the samples. Storing only the offsets may use less storage space than storing each sample's entire position. The offsets may be relative to bin coordinates or relative to positions on a regular grid. The sample position information stored in sample position memory 354 may be read by a dedicated sample position calculation unit (not shown) and processed to calculate example sample positions for graphics processor 90. More detailed information on sample position offsets is included below (see description of FIGS. 9 and 10).

In another embodiment, sample position memory 354 may be configured to store a table of random numbers. Sample position memory 354 may also comprise dedicated hardware to generate one or more different types of regular. grids. This hardware may be programmable. The stored random numbers may be added as offsets to the regular grid positions generated by the hardware. In one embodiment, the sample position memory may be programmable to access or "unfold" the random number table in a number of different ways. This may allow a smaller table to be used without visual artifacts caused by repeating sample position offsets. In one embodiment, the random numbers may be repeatable, thereby allowing draw process 352 and sample-to-pixel calculation process 360 to utilize the same offset for the same sample without necessarily storing each offset.

As shown in the figure, sample position memory 354 may be configured to store sample offsets generated according to a number of different schemes such as a regular square grid, a regular hexagonal grid, a perturbed regular grid; or a random (stochastic) distribution. Graphics system 112 may receive an indication from the operating system, device driver, or the geometry data 350 that indicates which type of sample positioning scheme is to be used. Thus the sample position memory 354 is configurable or programmable to generate position information according to one or more different schemes. More detailed information on several sample position schemes are described further below (see description of FIG. 8).

In one embodiment, sample position memory 354 may comprise a RAM/ROM that contains stochastic sample points (or locations) for different total sample counts per bin. As used herein, the term "bin" refers to a region or area in screen-space and contains however many samples are in that area (e.g., the bin may be 1×1 pixels in area, 2×2 pixels in area, etc.). The use of bins may simplify the storage and access of samples in sample buffer 162. A number of different bin sizes may be used (e.g., one sample per bin, four samples per bin, etc.). In the preferred embodiment, each bin has an xy-position that corresponds to a particular location on the display. The bins are preferably regularly spaced. In this embodiment the bins' xy-positions may be determined from the bin's storage location within sample buffer 162. The bins positions correspond to particular positions on the display. In some embodiments, the bin positions may correspond to pixel centers, while in other embodiments the bin positions correspond to points that are located between pixel centers. The specific position of each sample within a bin may be determined by looking up the sample's offset in the RAM/ROM table (the offsets may be stored relative to the corresponding bin position). However, depending upon the implementation, not all bin sizes may have a unique RAM/ROM entry. Some bin sizes may simply read a subset of the larger bin sizes' entries. In one embodiment, each supported size has at least four different sample position scheme variants, which may reduce final image artifacts due to repeating sample positions.

In one embodiment, position memory 354 may store pairs of 8-bit numbers, each pair comprising an x-offset and a y-offset (other possible offsets are also possible, e.g., a time offset, a z-offset, etc.). When added to a bin position, each pair defines a particular position in screen space. The term "screen space" refers generally to the coordinate system of the display device. To improve read times, memory 354 may be constructed in a wide/parallel manner so as to allow the memory to output more than one sample location per clock cycle.

Once the sample positions have been read from sample position memory 354, draw process 352 selects the samples positions that fall within the polygon currently being rendered. Draw process 352 then calculates the z and color information (which may include alpha or other depth of field information values) for each of these samples and stores the data into sample buffer 162. In one embodiment, the sample buffer may only single-buffer z values (and perhaps alpha values) while double buffering other sample components such as color. Unlike prior art systems, graphics system 112 may double buffer all samples (although not all sample components may be double-buffered, i.e., the samples may have components that are not double-buffered, or not all samples may be double-buffered). In one embodiment, the samples are stored into sample buffer 162 in bins. In some embodiments, the size of bins, i.e., the quantity of samples within a bin, may vary from frame to frame and may also vary across different regions of display device 84 within a single frame. For example, bins along the edges of display device may comprise only one sample, while bins corresponding to pixels near the center of display device 84 may comprise sixteen samples. Note the area of bins may vary from region to region. The use of bins will be described in greater detail below in connection with FIG. 11.

In parallel and independently of draw process 352, filter process 360 is configured to read samples from sample buffer 162, filter (i.e., filter) them, and then output the resulting output pixel to display device 84. Sample-to-pixel calculation units 170 implement filter process 380. Thus, for at least a subset of the output pixels, the filter process is operable to filter a plurality of samples to produce a respective output pixel. In one embodiment, filter process 360 is configured to: (i) determine the distance from each sample to the center of the output pixel being filtered; (ii) multiply the sample's components (e.g., color and alpha) with a filter value that is a specific (programmable) function of the distance; (iii) sum all the weighted samples that contribute to the output pixel, and (iv) normalize the resulting output pixel. The filter process 360 is described in greater detail below (see description accompanying FIGS. 11, 12, and 14). Note the extent of the filter need not be circular (i.e., it may be a function of x and y instead of the distance), but even if the extent is, the filter need not be circularly symmetrical. The filter's "extent" is the area within which samples can influence the particular pixel being calculated with the filter.

Figure 7:
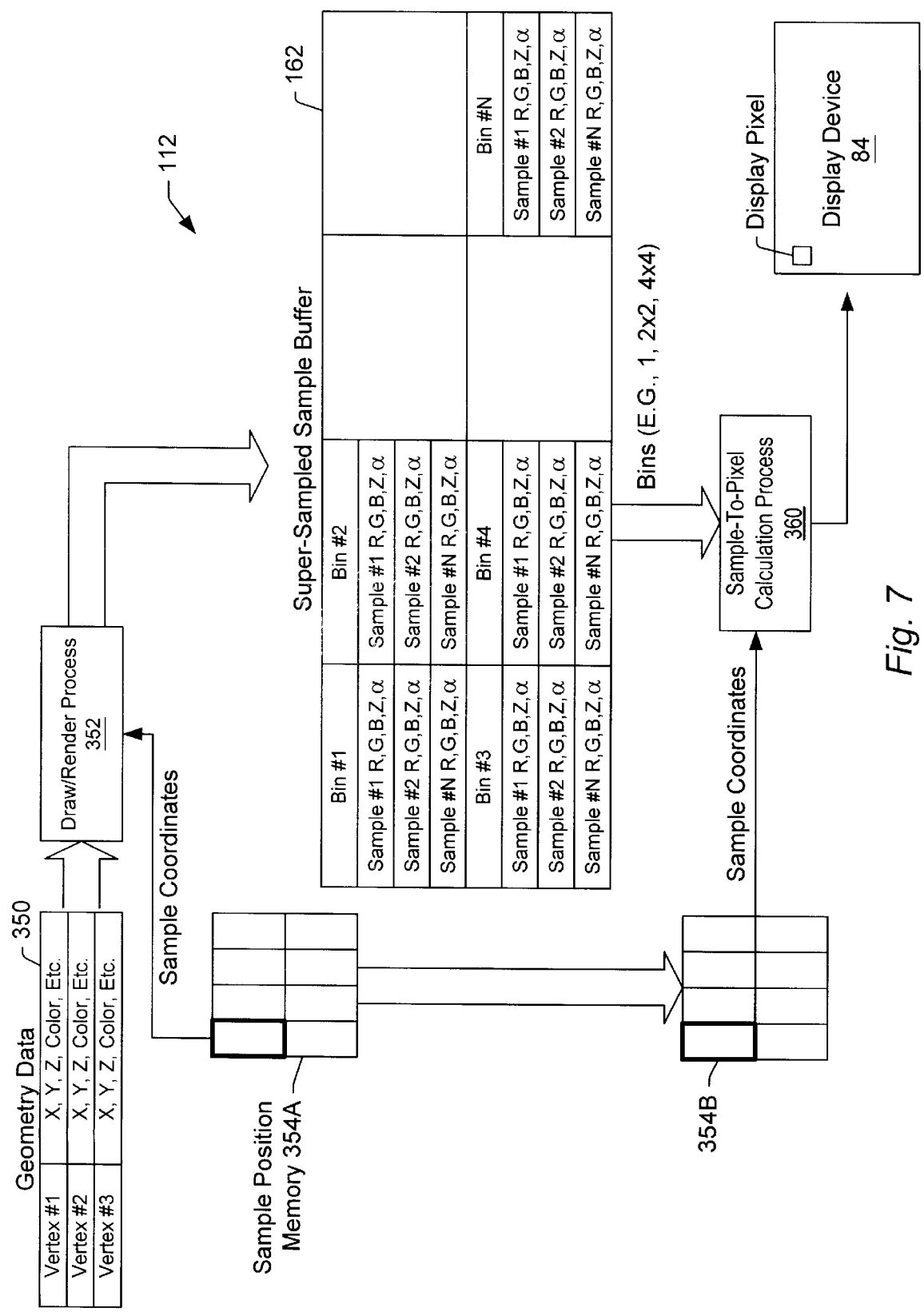
FIG. 7 is a diagram illustrating details of another embodiment of a graphics system having one embodiment of a variable resolution super-sampled sample buffer.

Turning now to FIG. 7, a diagram illustrating an alternate embodiment of graphics system 112 is shown. In this embodiment, two or more sample position memories 354A and 354B are utilized. Thus, the sample position memories 354A–B are essentially double-buffered. If the sample positions are kept the same from frame to frame, then the sample positions may be single buffered. However, if the sample positions may vary from frame to frame, then graphics system 112 may be advantageously configured to double-buffer the sample positions. The sample positions may be double buffered on the rendering side (i.e., memory 354A may be double buffered) and or the filter/convolve side (i.e., memory 354B may be double buffered). Other combinations are also possible. For example, memory 354A may be single-buffered, while memory 354B is doubled buffered. This configuration may allow one side of memory 354B to be used for refreshing (i.e., by filter/convolve process 360) while the other side of memory 354B is used being updated. In this configuration, graphics system 112 may change sample position schemes on a per-frame basis by shifting the sample positions (or offsets) from memory 354A to double-buffered memory 354B as each frame is rendered. Thus, the positions used to calculate the samples (read from memory 354A) are copied to memory 354B for use during the filtering process (i.e., the sample-to-pixel conversion process). Once the position information has been copied to memory 354B, position memory 354A may then be loaded with new sample position offsets to be used for the second frame to be rendered. In this way the sample position information follows the samples from the draw/render process to the filter process.

Yet another alternative embodiment may store tags to offsets with the samples themselves in super-sampled sample buffer 162. These tags may be used to look-up the offset/perturbation associated with each particular sample.

Sample Positioning Schemes

FIG. 8 illustrates a number of different sample positioning schemes. In regular grid positioning scheme 190, each sample is positioned at an intersection of a regularly-spaced grid. Note however, that as used herein the term "regular grid" is not limited to square grids. Other types of grids are also considered "regular" as the term is used herein, including, but not limited to, rectangular grids, hexagonal grids, triangular grids, logarithmic grids, and semi-regular lattices such as Penrose tiling.

Perturbed regular grid positioning scheme 192 is based upon the previous definition of a regular grid. However, the samples in perturbed regular grid scheme 192 may be offset from their corresponding grid intersection. In one embodiment, the samples may be offset by a random angle (e.g., from 0° to 360°) and a random distance, or by random x and y offsets, which may or may not be limited to a predetermined range. The offsets may be generated in a number of ways, e.g., by hardware based upon a small number of seeds, looked up from a table, or by using a pseudo-random function. Once again, perturbed regular grid scheme 192 may be based on any type of regular grid (e.g., square, or hexagonal). A rectangular or hexagonal perturbed grid may be particularly desirable due to the geometric properties of these grid types.

Stochastic sample positioning scheme 194 represents a third potential type of scheme for positioning samples. Stochastic sample positioning involves randomly distributing the samples across a region (e.g., the displayed region on a display device or a particular window). Random positioning of samples may be accomplished through a number of different methods, e.g., using a random number generator such as an internal clock to generate pseudo-random numbers. Random numbers or positions may also be pre-calculated and stored in memory.

Figure 9:
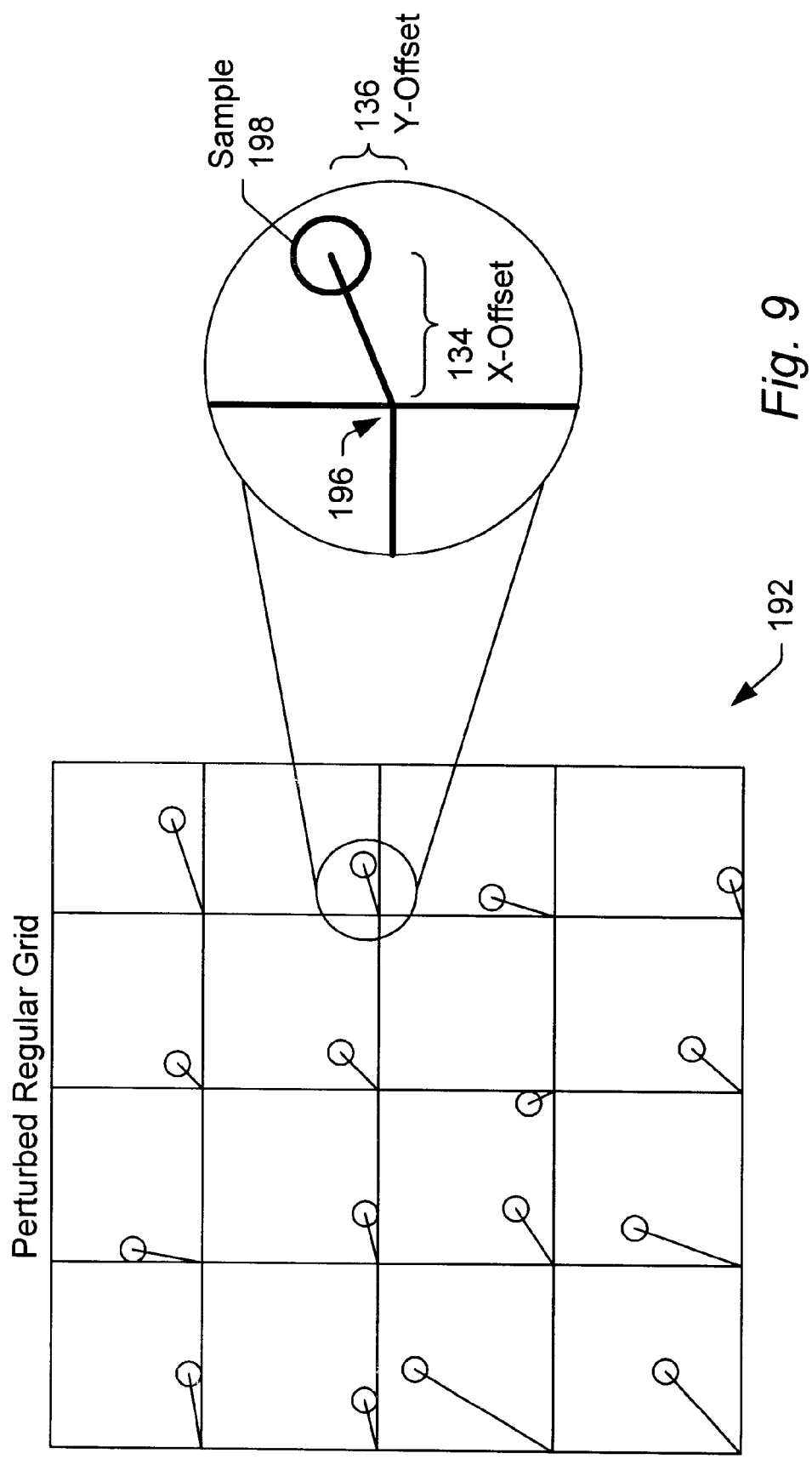
FIG. 9 is a diagram illustrating details of one embodiment of a sample positioning scheme.

Turning now to FIG. 9, details of one embodiment of perturbed regular grid scheme 192 are shown. In this embodiment, samples are randomly offset from a regular square grid by x- and y-offsets. As the enlarged area shows, sample 198 has an x-offset 134 that specifies its horizontal displacement from its corresponding grid intersection point 196. Similarly, sample 198 also has a y-offset 136 that specifies its vertical displacement from grid intersection point 196. The random offset may also be specified by an angle and distance. As with the previously disclosed embodiment that utilized angles and distances, x-offset 134 and y-offset 136 may be limited to a particular minimum and or maximum value or range of values.

Figure 10:
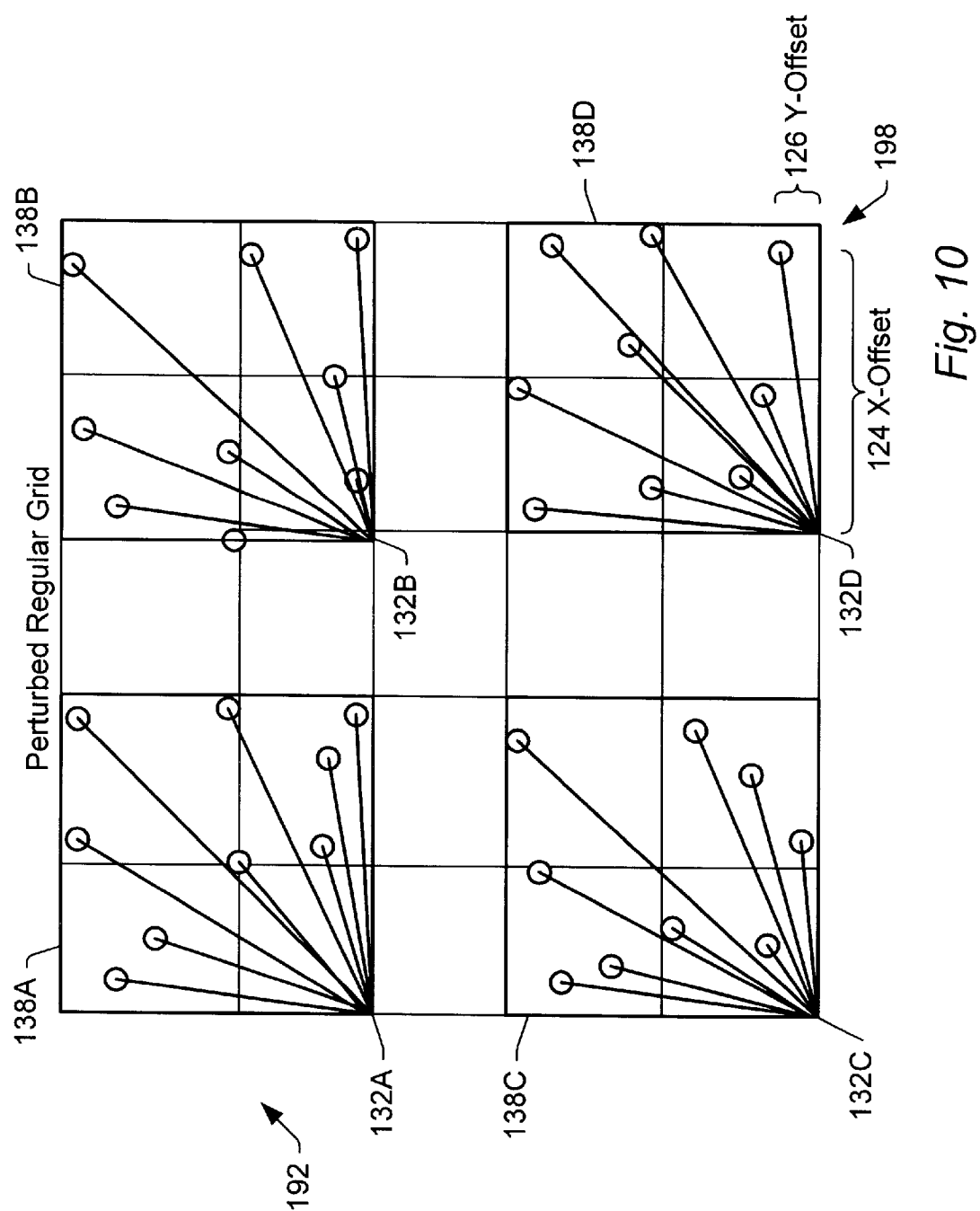
FIG. 10 is a diagram illustrating details of another embodiment of a sample positioning scheme.

Turning now to FIG. 10, details of another embodiment of perturbed regular grid scheme 192 are shown. In this embodiment, the samples. are grouped into "bins" 138A–D. In this embodiment, each bin comprises nine (i.e., 3×3) samples. Different bin sizes may be used in other embodiments (e.g., bins storing 2×2 samples or 4×4 samples). In the embodiment shown, each sample's position is determined as an offset relative to the position of the bin. The position of the bins may be defined as any convenient position related to the grid, e.g., the lower left-hand corners 132A–D as shown in the figure. For example, the position of sample 198 is determined by summing x-offset 124 and y-offset 126 to the x and y coordinates of the corner 132D of bin 138D. As previously noted, this may reduce the size of the sample position memory used in some embodiments.

Figure 11:
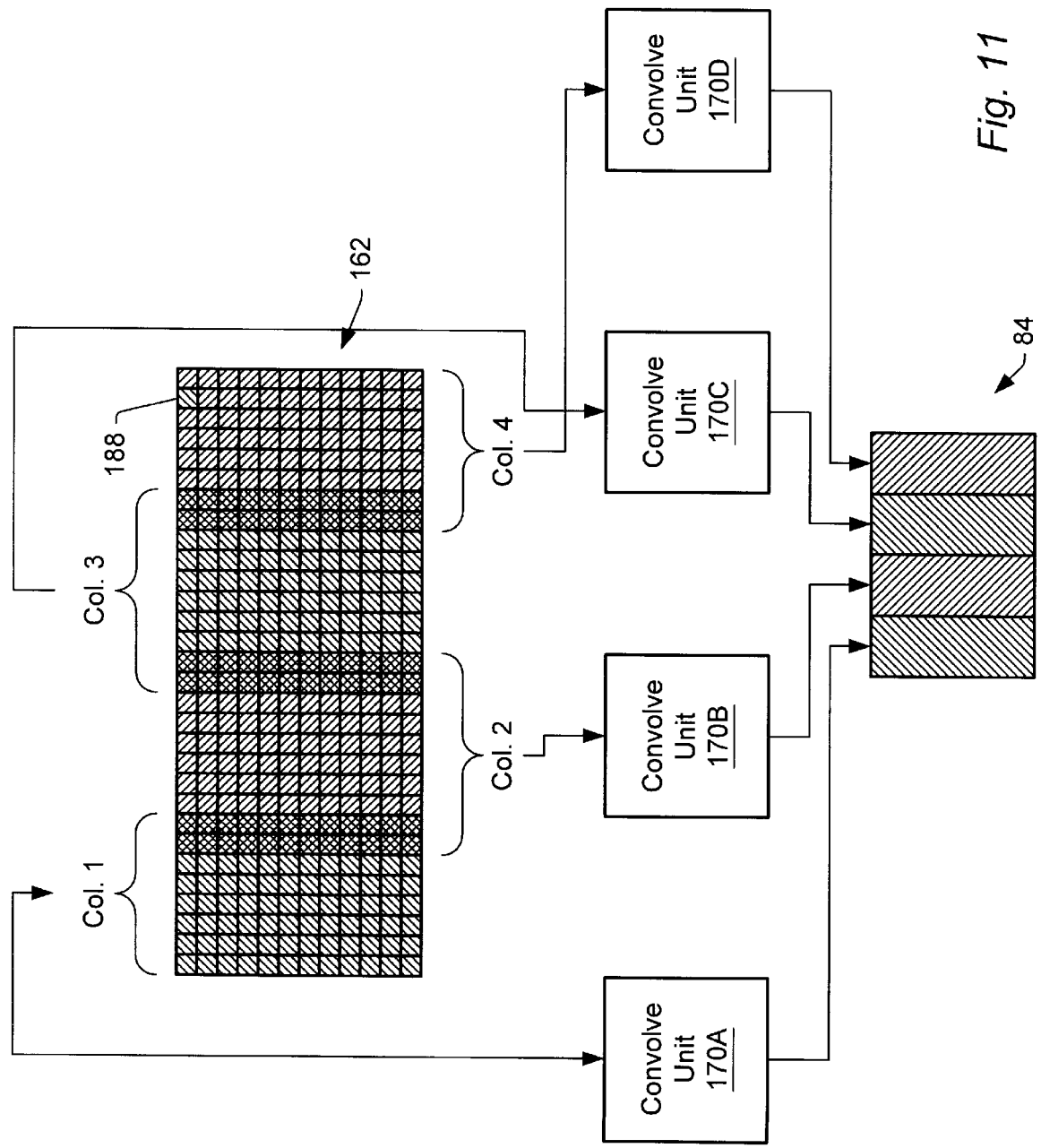
FIG. 11 is a diagram illustrating details of method of converting samples to pixels in parallel.

Turning now to FIG. 11, one possible method for rapidly converting samples stored in sample buffer 162 into pixels is shown. In this embodiment, the contents of sample buffer 162 are organized into columns (e.g., Cols. 1–4). Each column in sample buffer 162 may comprise a two-dimensional array of bins. The columns may be configured to horizontally overlap (e.g., by one or more bins), and each column may be assigned to a particular sample-to-pixel calculation unit 170A–D for the convolution process. The amount of the overlap may depend upon the extent of the filter being used. The example shown in the figure illustrates an overlap of two bins (each square such as square 188 represents a single bin comprising one or more samples). Advantageously, this configuration may allow sample-to-pixel calculation units 170A–D to work independently and in parallel, with each sample-to-pixel calculation unit 170A–D receiving and converting its own column. Overlapping the columns will eliminate visual bands or other artifacts appearing at the column boundaries for any operators larger than a pixel in extent.

Figure 11A:
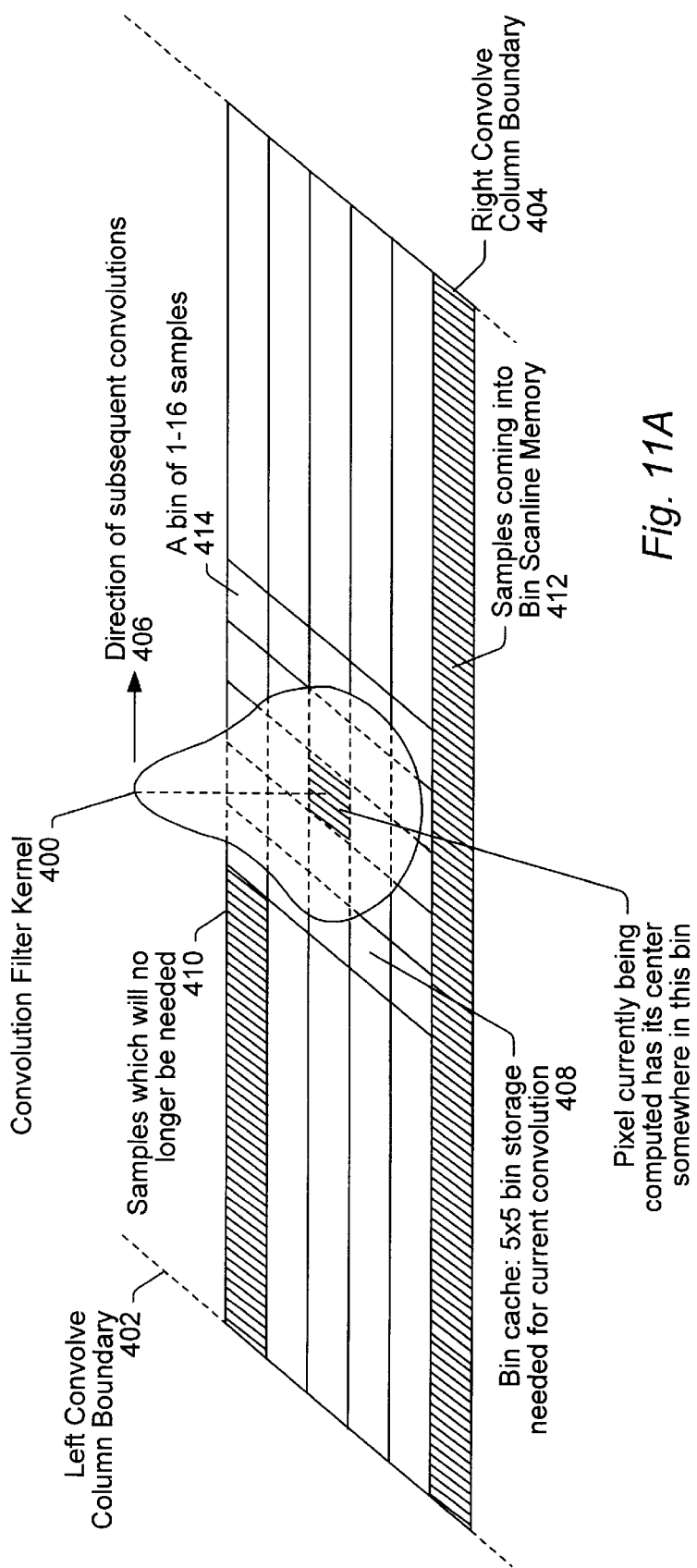
FIG. 11A is a diagram illustrating more details of the embodiment from FIG. 11.

Turning now to FIG. 11A, more details of one embodiment of a method for reading the samples from a super-sampled sample buffer are shown. As the figure illustrates, the convolution filter kernel 400 travels across column 414 (see arrow 406) to generate output pixels. One or more sample-to-pixel calculation units 170 may implement the convolution filter kernel 400. A bin cache 408 may used to provide quick access to the samples that may potentially contribute to the output pixel. As the convolution process proceeds, bins are read from the super-sampled sample buffer and stored in bin cache 408. In one embodiment, bins that are no longer needed 410 are overwritten in the cache by new bins 412. As each pixel is generated, convolution filter kernel 400 shifts. Kernel 400 may be visualized as proceeding in a sequential fashion within the column in the direction indicated by arrow 406. When kernel 400 reaches the end of the column, it may shift down one or more rows of samples and then proceed again. Thus the convolution process proceeds in a scan line manner, generating one column of output pixels for display.

Figure 11B:
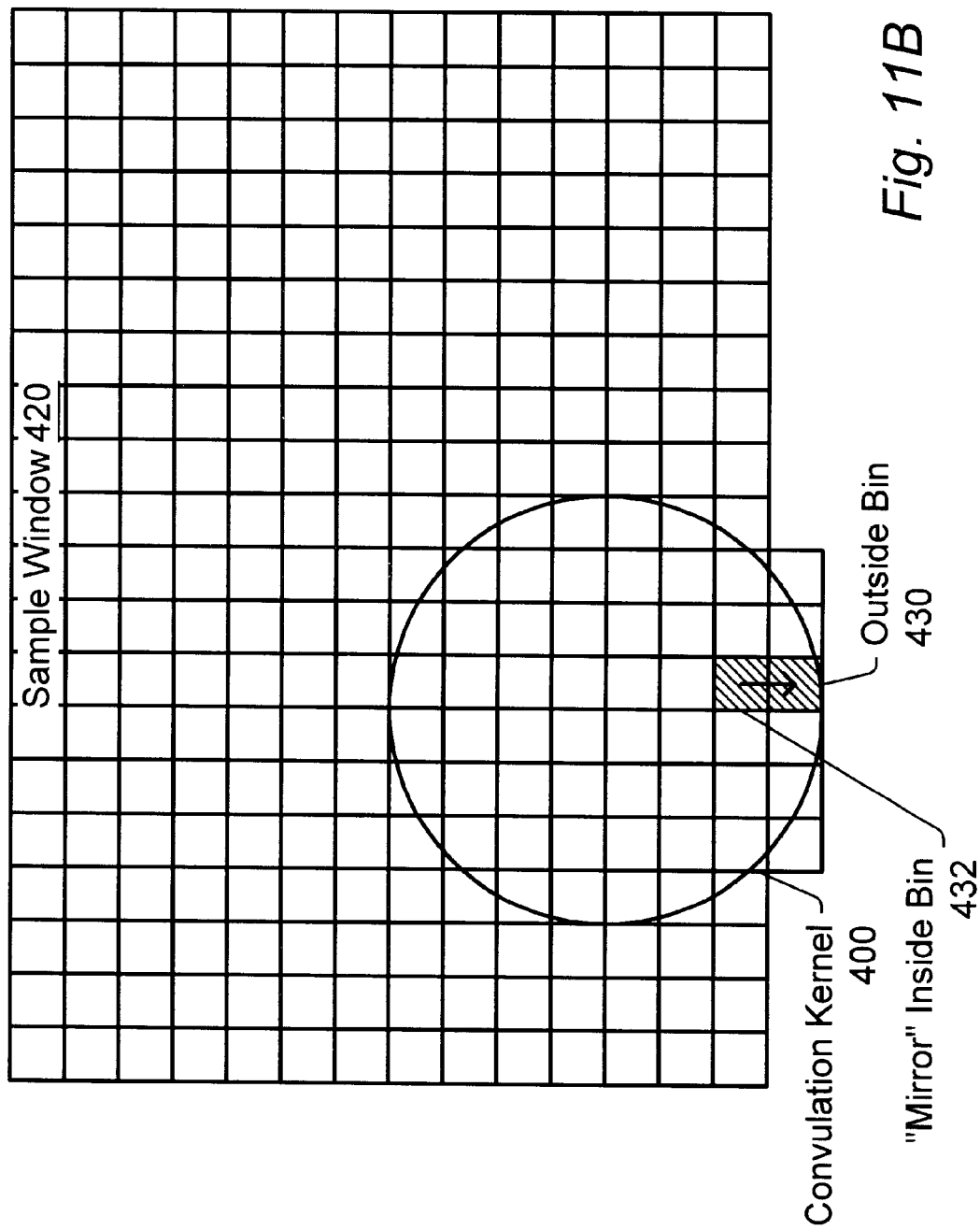
FIG. 11B is a diagram illustrating details of one embodiment of a method for dealing with boundary conditions.

Turning now to FIG. 11B, a diagram illustrating potential border conditions is shown. In one embodiment, the bins that fall outside of sample window 420 may be replaced with samples having predetermined background colors specified by the user. In another embodiment, bins that fall outside the window are not used by setting their weighting factors to zero (and then dynamically calculating normalization coefficients). In yet another embodiment, the bins at the inside edge of the window may be duplicated to replace those outside the window. This is indicated by outside bin 430 being replaced by mirror inside bin 432.

Figure 12:
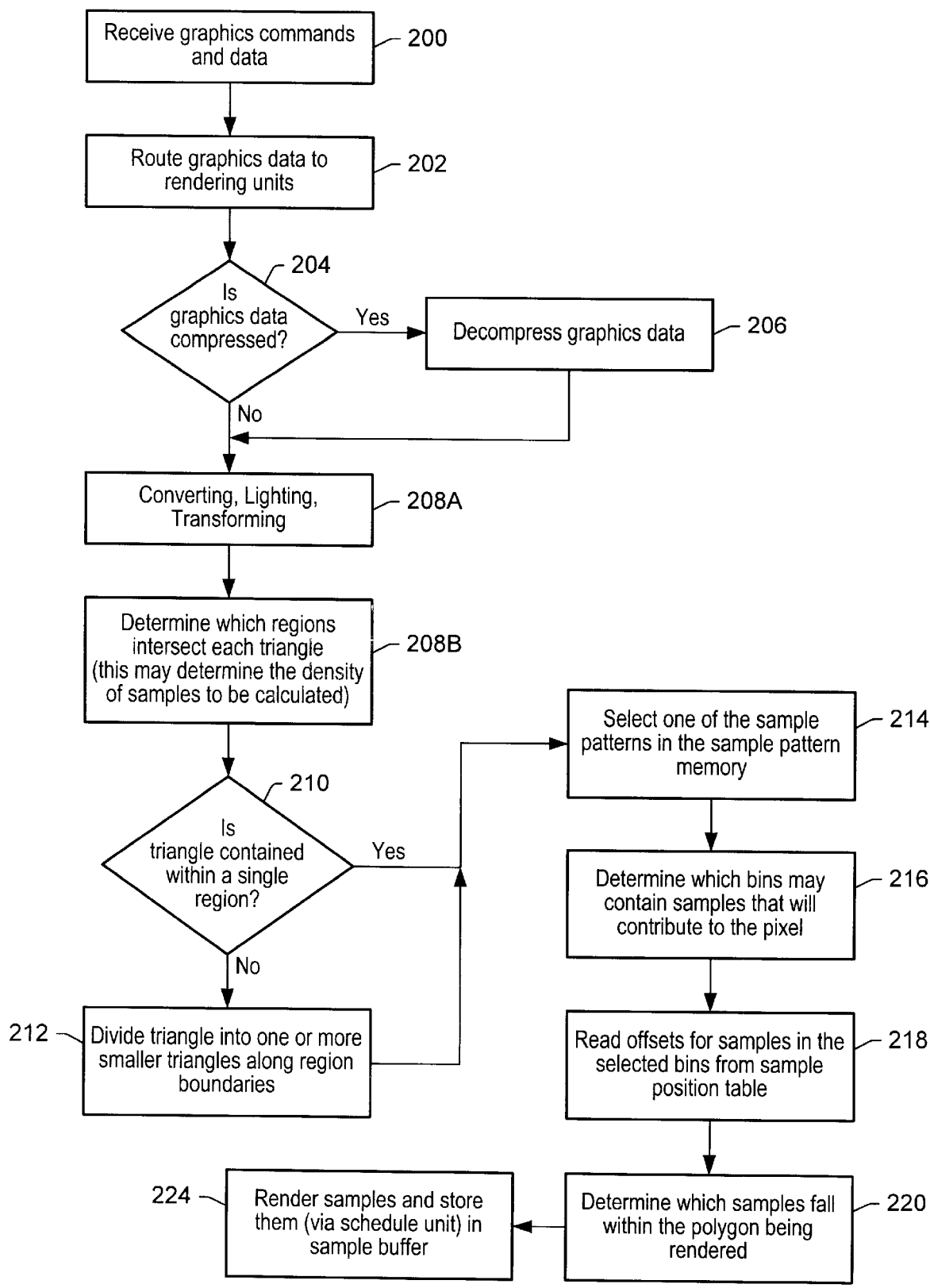
FIG. 12 is a flowchart illustrating one embodiment of a method for drawing samples into a super-sampled sample buffer.

FIG. 12 is a flowchart of one embodiment of a method for drawing or rendering sample pixels into a super-sampled sample buffer. Certain of the steps of FIG. 12 may occur concurrently or in different orders. In this embodiment, the graphics system receives graphics commands and graphics data from the host CPU 102 or directly from main memory 106 (step 200). Next, the instructions and data are routed to one or more rendering units 150A–D (step 202). If the graphics data is compressed (step 204), then the rendering units 150A–D decompress the data into a useable format, e.g., triangles (step 206). Next, the triangles are processed, e.g., converted to screen space, lit, and transformed (step 208A). If the graphics system implements variable resolution super sampling, then the triangles are compared with the sample density region boundaries (step 208B). In variable-resolution super-sampled sample buffer implementations, different regions of the display device may be allocated different sample densities based upon a number of factors (e.g., the center of the attention on-the screen as determined by eye or head tracking). Sample density regions are described in greater detail below (see section entitled Variable Resolution Sample buffer below). If the triangle crosses a region boundary (step 210), then the triangle may be divided into two smaller polygons along the region boundary (step 212). This may allow each newly formed triangle to have a single sample density. In one embodiment, the graphics system may be configured to simply use the entire triangle twice (i.e., once in each region) and then use a bounding box to effectively clip the triangle.

Next, one of the sample position schemes (e.g., regular grid, perturbed regular grid, or stochastic) are selected from the sample position memory 184 (step 214). The sample position scheme will generally have been pre-programmed into the sample position memory 184, but may also be selected "on the fly". Based upon this sample position scheme and the sample density of the region containing the triangle, rendering units 150A–D determine which bins may contain samples located within the triangle's boundaries (step 216). The offsets for the samples within these bins are then read from sample position memory 184 (step 218). Each sample's position is then calculated using the offsets and is compared with the triangle's vertices to determine if the sample is within the triangle (step 220). Step 220 is discussed in greater detail below.

For each sample that is determined to be within the triangle, the rendering unit draws the sample by calculating the sample's color, alpha and other attributes. This may involve lighting calculation and interpolation based upon the color and texture map information associated with the vertices of the triangle. Once the sample is rendered, it may be forwarded to schedule unit 154, which then stores the sample in sample buffer 162 (step 224).

Note the embodiment of the method described above is used for explanatory purposes only and is not meant to be limiting. For example, in some embodiments the steps shown in the figure as occurring serially may be implemented in parallel. Furthermore, some steps may be reduced or eliminated in certain embodiments of the graphics system (e.g., steps 204–206 in embodiments that do not implement geometry compression or steps 210–212 in embodiments that do not implement a variable resolution super-sampled sample buffer).

Determination of which Samples Reside within the Polygon Being Rendered

The comparison may be performed in a number of different ways. In one embodiment, the deltas between the three vertices defining the triangle are first determined. For example, these deltas may be taken in the order of first to second vertex (v2–v1)=d12, second to third vertex (v3–v2)= d23, and third vertex back to the first vertex (v1–v3)=d31. These deltas form vectors, and each vector may be categorized as belonging to one of the four quadrants of the coordinate plane (e.g., by using the two sign bits of its delta X and Y coefficients). A third condition may be added determining whether the vector is an X-major vector or Y-major vector. This may be determined by calculating whether abs(delta$_{13}$x) is greater than abs(delta$_{13}$y).

Figure 12A:
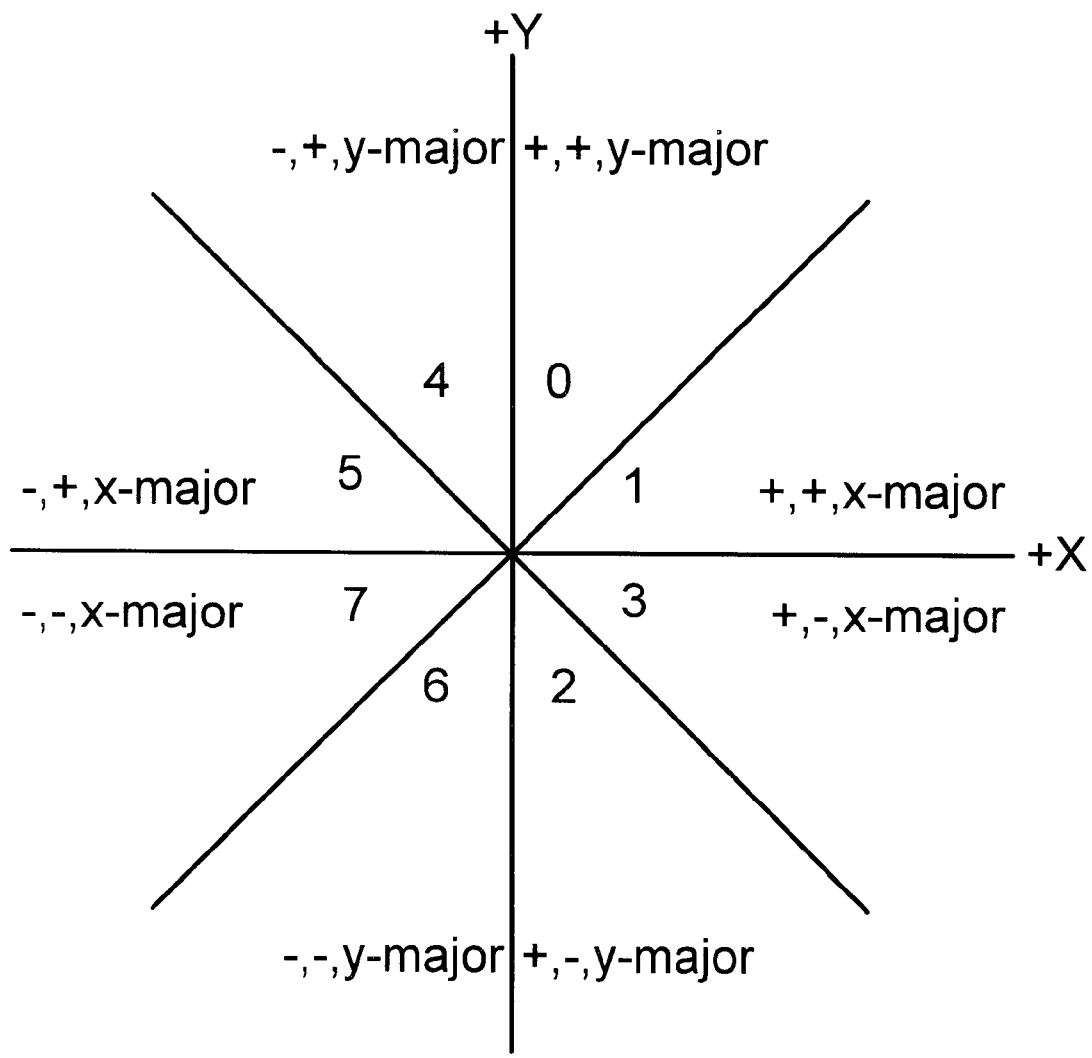
FIG. 12A is a diagram illustrating one embodiment for coding triangle vertices.

Using these three bits of information, the vectors may each be categorized as belonging to one of eight different regions of the coordinate plane. If three bits are used to define these regions, then the X-sign bit (shifted left by two), the Y-sign bit (shifted left by one), and the X-major bit, may be used to create the eight regions as shown in FIG. 12A.

Next, three edge equations may be used to define the inside portion of the triangle. These edge equations (or half-plane equations) may be defined using slope-intercept form. To reduce the numerical range needed, both X-major and Y-major equation forms may be used (such that the absolute value of the slope value may be in the range of 0 to 1). Thus, the two edge equations are:

X-major: $y-m\cdot x-b<0$, when the point is below the line

Y-major: $x-m\cdot y-b<0$, when the point is to the left of the line

The X-major equations produces a negative versus positive value when the point in question is below the line, while the Y-major equation produces a negative versus positive value when the point in question is to the left of the line. Since which side of the line is the "accept" side is known, the sign bit (or the inverse of the sign bit) of the edge equation result may be used to determine whether the sample is on the "accept" side or not. This is referred to herein as the "accept bit". Thus, a sample is on the accept side of a line if:

X-major: (y–m–x·b<0)<xor>accept
Y-major: (x–m–y·b<0)<xor>accept

The accept bit may be calculated according to the following table, wherein cw designates whether the triangle is clockwise (cw=1) or counter-clockwise (cw=0):

1:accept=!cw
0:accept=cw
4:accept=cw
5:accept=cw
7:accept=cw
6:accept=!cw
2:accept=!cw
3:accept=!cw Tie breaking rules for this representation may also be implemented (e.g., coordinate axes may be defined as belonging to the positive octant). Similarly, X-major may be defined as owning all points that tie on the slopes.

In an alternate embodiment, the accept side of an edge may be determined by applying the edge equation to the third vertex of the triangle (the vertex that is not one of the two vertices forming the edge). This method may incur the additional cost of a multiply-add, which may not be used by the technique described above.

To determine the "faced-ness" of a triangle (i.e., whether the triangle is clockwise or counter-clockwise), the delta-directions of two edges of the triangle may be checked and the slopes of the two edges may be compared. For example, assuming that edge12 has a delta-direction of 1 and the second edge (edge23) has a delta-direction of 0,4, or 5, then the triangle is counter-clockwise. If, however, edge23 has a delta-direction of 3,2, or 6, then the triangle is clockwise. If edge23 has a delta-direction of 1 (i.e., the same as edge12), then comparing the slopes of the two edges breaks the tie (both are x-major). If edge12 has a greater slope,then the triangle is counter-clockwise. If edge23 has a delta-direction of 7 (the exact opposite of edge12), then again the slopes are compared, but with opposite results in terms of whether the triangle is clockwise or counter-clockwise.

The same analysis can be exhaustively applied to all combinations of edge12 and edge23 delta-directions, in every case determining the proper faced-ness. If the slopes are the same in the tie case, then the triangle is degenerate (i.e., with no interior area). It can be explicitly tested for and culled, or, with proper numerical care, it could be let through as it will cause no pixels to render. One special case is when a triangle splits the view plane, but that may be detected earlier in the pipeline (e.g., when front plane and back plane clipping are performed).

Note in most cases only one side of a triangle is rendered. Thus, after the faced-ness of a triangle is determined, if the face is the one to be rejected, then the triangle can be culled (i.e., subject to no further processing with no pixels generated). Further note that this determination of faced-ness only uses one additional comparison (i.e., of the slope of edge12 to that of edge23) beyond factors already computed. Many traditional approaches may utilize more complex computation (though at earlier stages of the set-up computation).

Figure 13:
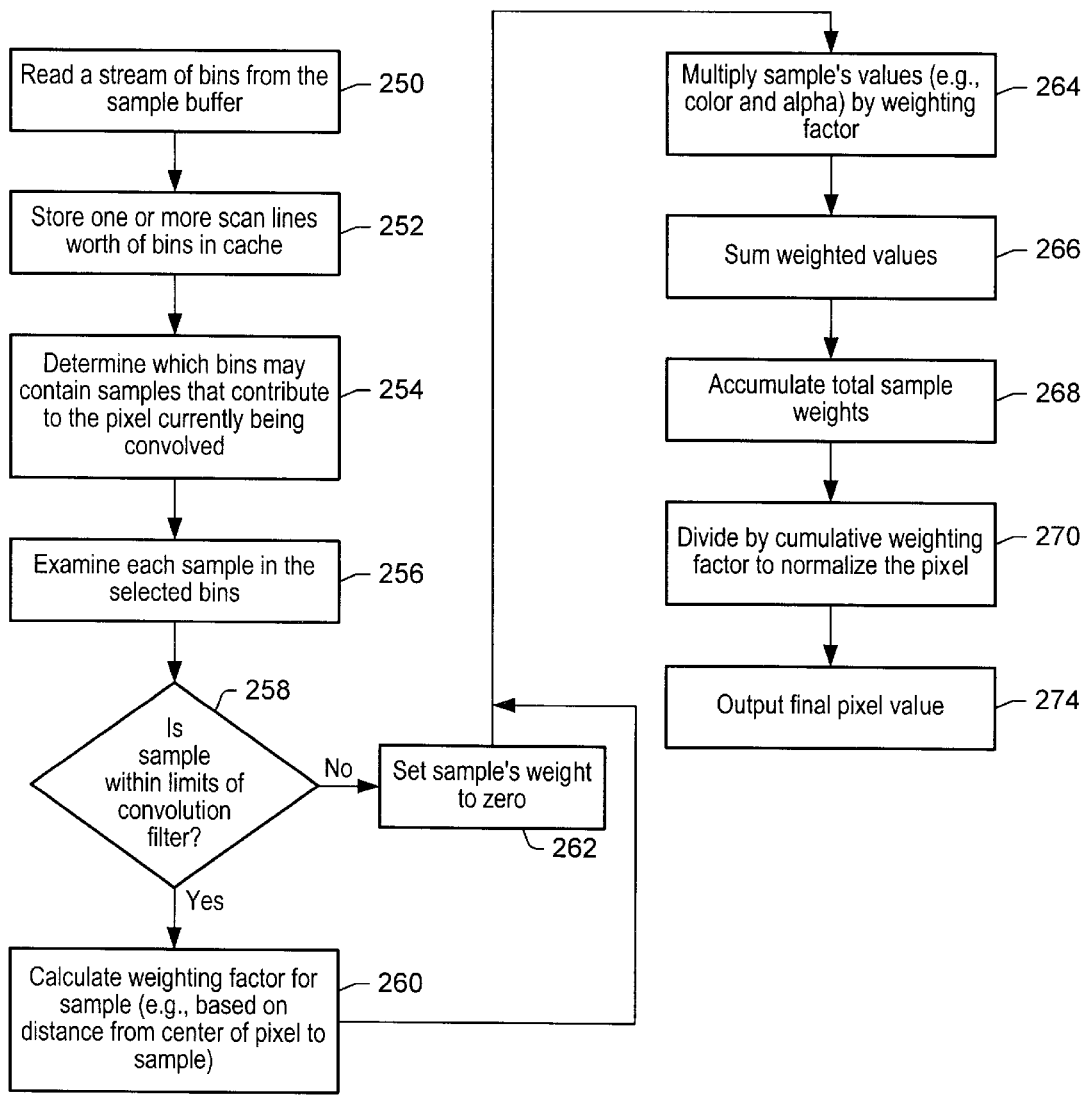
FIG. 13 is a diagram illustrating one embodiment of a method for calculating pixels from samples.

FIG. 13 is a flowchart of one embodiment of a method for filtering samples stored in the super-sampled sample buffer to generate output pixels. First, a stream of bins are read from the super-sampled sample buffer (step 250). These may be stored in one or more caches to allow the sample-to-pixel calculation units 170 easy access during the convolution process (step 252). Next, the bins are examined to determine which may contain samples that contribute to the output pixel currently being generated by the filter process (step 254). Each sample that is in a bin that may contribute to the output pixel is then individually examined to determine if the sample does indeed contribute (steps 256–258). This determination may be based upon the distance from the sample to the center of the output pixel being generated.

In one embodiment, the sample-to-pixel calculation units 170 may be configured to calculate this distance (i.e., the extent of the filter at sample's position) and then use it to index into a table storing filter weight values according to filter extent (step 260). In another embodiment, however, the potentially expensive calculation for determining the distance from the center of the pixel to the sample (which typically involves a square root function) is avoided by using distance squared to index into the table of filter weights. Alternatively, a function of x and y may be used in lieu of one dependent upon a distance calculation. In one embodiment, this may be accomplished by utilizing a floating point format for the distance (e.g., four or five bits of mantissa and three bits of exponent), thereby allowing much of the accuracy to be maintained while compensating for the increased range in values. In one embodiment, the table may be implemented in ROM. However, RAM tables may also be used. Advantageously, RAM tables may, in some embodiments, allow the graphics system to vary the filter coefficients on a per-frame basis. For example, the filter coefficients may be varied to compensate for known shortcomings of the display or for the user's personal preferences. The graphics system can also vary the filter coefficients on a screen area basis within a frame, or on a per-output pixel basis. Another alternative embodiment may actually calculate the desired filter weights for each sample using specialized hardware (e.g., multipliers and adders). The filter weight for samples outside the limits of the convolution filter may simply be multiplied by a filter weight of zero (step 262), or they may be removed from the calculation entirely.

Once the filter weight for a sample has been determined, the sample may then be multiplied by its filter weight (step 264). The weighted sample may then be summed with a running total to determine the final output pixel's color value (step 266). The filter weight may also be added to a running total pixel filter weight (step 268), which is used to normalize the filtered pixels. Normalization advantageously prevents the filtered pixels (e.g., pixels with more samples than other pixels) from appearing too bright or too dark by compensating for gain introduced by the convolution process. After all the contributing samples have been weighted and summed, the total pixel filter weight may be used to divide out the gain caused by the filtering (step 270). Finally, the normalized output pixel may be output for gamma correction, digital-to-analog conversion (if necessary), and eventual display (step 274).

Figure 14:
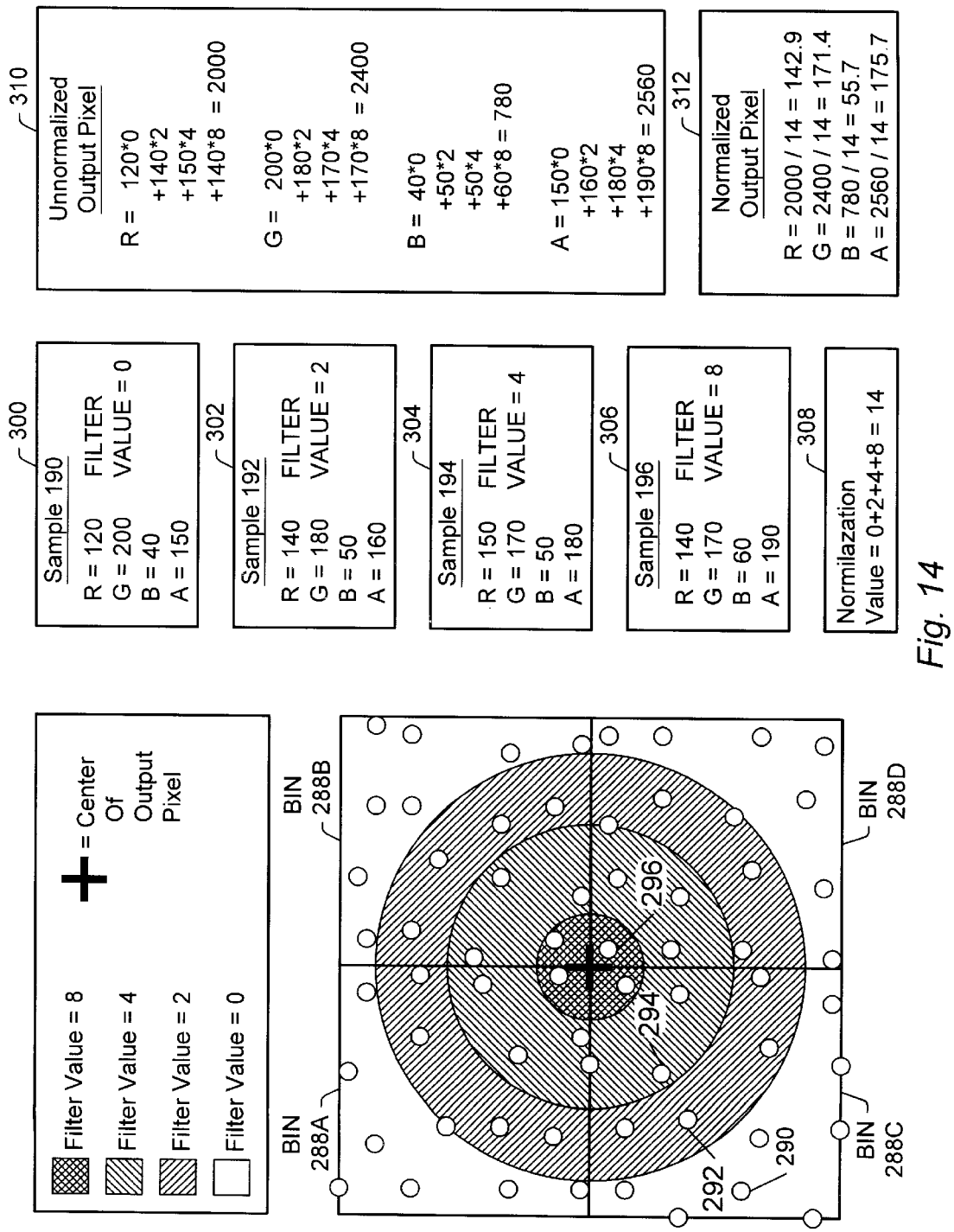
FIG. 14 is a diagram illustrating details of one embodiment of a pixel convolution for an example set of samples.

FIG. 14 illustrates a simplified example of an output pixel convolution. As the figure shows, four bins 288A–D contain samples that may possibly contribute to the output pixel. In this example, the center of the output pixel is located at the boundary of bins 288A–288D. Each bin comprises sixteen samples, and an array of 2 four bins (2×2) is filtered to generate the output pixel. Assuming circular filters are used, the distance of each sample from the pixel center determines which filter value will be applied to the sample. For example, sample 296 is relatively close to the pixel center, and thus falls within the region of the filter having a filter value of 8. Similarly, samples 294 and 292 fall within the regions of the filter having filter values of 4 and 2, respectively. Sample 290, however, falls outside the maximum filter extent, and thus receives a filter value of 0. Thus sample 290 will not contribute to the output pixel's value. This type of filter ensures that the samples located the closest to the pixel center will contribute the most, while pixels located the far from the pixel center will contribute less to the final output pixel values. This type of filtering automatically performs anti-aliasing by smoothing any abrupt changes in the image (e.g., from a dark line to a light background). Another particularly useful type of filter for anti-aliasing is a windowed sinc filter. Advantageously, the windowed sinc filter contains negative lobes that resharpen some of the blended or "fuzzed" image. Negative lobes are areas where the filter causes the samples to subtract from the pixel being calculated. In contrast samples on either side of the negative lobe add to the pixel being calculated.

Example values for samples 290–296 are illustrated in boxes 300–308. In this example, each sample comprises red, green, blue and alpha values, in addition to the sample's positional data. Block 310 illustrates the calculation of each pixel component value for the non-normalized output pixel. As block 310 indicates, potentially undesirable gain is introduced into the final pixel values (i.e., an out pixel having a red component value of 2000 is much higher than, any of the sample's red component values). As previously noted, the filter values may be summed to obtain normalization value 308. Normalization value 308 is used to divide out the unwanted gain from the output pixel. Block 312 illustrates this process and the final normalized example pixel values.

Note the values used herein were chosen for descriptive purposes only and are not meant to be limiting. For example, the filter may have a large number of regions each with a different filter value. In one embodiment, some regions may have negative filter values. The filter utilized may be a continuous function that is evaluated for each sample based on the sample's distance from the pixel center. Also note that floating point values may be used for increased precision. A variety of filters may be utilized, e.g., cylinder, cone, gaussian, Katmull-Rom, windowed sinc, Mitchell filter, box, tent.

Full-Screen Anti-aliasing

The vast majority of current 3D graphics systems only provide real-time anti-aliasing for lines and dots. While some systems also allow the edge of a polygon to be "fuzzed", this technique typically works best when all polygons have been pre-sorted in depth. This may defeat the purpose of having general-purpose 3D rendering hardware for most applications (which do not depth pre-sort their polygons). In one embodiment, graphics system 112 may be configured to implement full-screen anti-aliasing by stochastically sampling up to sixteen samples per output pixel, filtered by a 4×4 convolution filter.

Variable Resolution Super-Sampling

Currently, the straight-forward brute force method of utilizing a fixed number of samples per pixel location, e.g., an 8x super-sampled sample buffer, would entail the use of eight times more memory, eight times the fill rate (i.e., memory bandwidth), and a convolution pipe capable of processing eight samples per pixel. Given the high resolution and refresh rates of current displays, a graphics system of this magnitude may be relatively expense to implement given today's level of integration.

In one embodiment, graphics system 112 may be configured to overcome these potential obstacles by implementing variable resolution super-sampling. In this embodiment, graphics system 112 mimics the human eye's characteristics by allocating a higher number of samples per pixel at one or more first locations on the screen (e.g., the point of foveation on the screen), with a drop-off in the number of samples per pixel for one or more second locations on the screen (e.g., areas farther away from the point of foveation). Depending upon the implementation, the point of foveation may be determined in a variety of ways. In one embodiment, the point of foveation may be a predetermined area around a certain object displayed upon the screen. For example, the area around a moving cursor or the main character in a computer game may be designated the point of foveation. In another embodiment, the point of foveation on the screen may be determined by head-tracking or eye-tracking. Even if eye/head/hand-tracking, cursor-based, or main character-based points of foveation are not implemented, the point of foveation may be fixed at the center of the screen, where the majority of viewer's attention is focused the majority of the time. Variable resolution super-sampling is described in greater detail below.

Variable-Resolution Super-Sampled Sample Buffer—FIGS. 15–19

A traditional frame buffer is one rectangular array of uniformly sampled pixels. For every pixel on the final display device (CRT or LCD), there is a single pixel or location of memory storage in the frame buffer (perhaps double buffered). There is a trivial one-to-one correspondence between the 2D memory address of a given pixel and its 2D sample address for the mathematics of rendering. Stated another way, in a traditional frame buffer there is no separate notion of samples apart from the pixels themselves. The output pixels are stored in a traditional frame buffer in a row/column manner corresponding to how the pixels are provided to the display during display refresh.

In a variable-resolution super-sampled sample buffer, the number of computed samples per output pixel varies on a regional basis. Thus, output pixels in regions of greater interest are computed using a greater number of samples, thus producing greater resolution in this region, and output pixels in regions of lesser interest are computed using a lesser number of samples, thus producing lesser resolution in this region.

As previously noted, in some embodiments graphic system 112 may be configured with a variable resolution super-sampled sample buffer. To implement variable resolution super-sampling, sample buffer 162 may be divided into smaller pieces, called regions. The size, location, and other attributes of these regions may be configured to vary dynamically, as parameterized by run-time registers on a per-frame basis.

Figure 15:
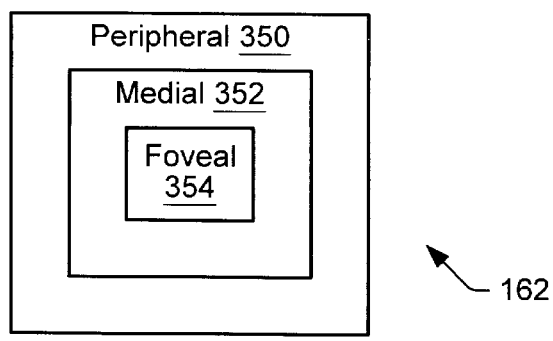
FIG. 15 is a diagram illustrating one embodiment of a method for dividing a super-sampled sample buffer into regions.

Turning now to FIG. 15, a diagram of one possible scheme for dividing sample buffer 162 is shown. In this embodiment, sample buffer 162 is divided into the following three nested regions: foveal region 354, medial region 352, and peripheral region 350. Each of these regions has a rectangular shaped outer border, but the medial and the peripheral regions have a rectangular shaped hole in their center. Each region may be configured with certain constant (per frame) properties, e.g., a constant density sample density and a constant size of pixel bin. In one embodiment, the total density range may be 256, i.e., a region could support between one sample every 16 screen pixels (4×4) and 16 samples for every 1 screen pixel. In other embodiments, the total density range may be limited to other values, e.g., 64. In one embodiment, the sample density varies, either linearly or non-linearly, across a respective region. Note in other embodiments the display may be divided into a plurality of constant sized regions (e.g., squares that are 4×4 pixels in size or 40×40 pixels in size).

Figure 16:
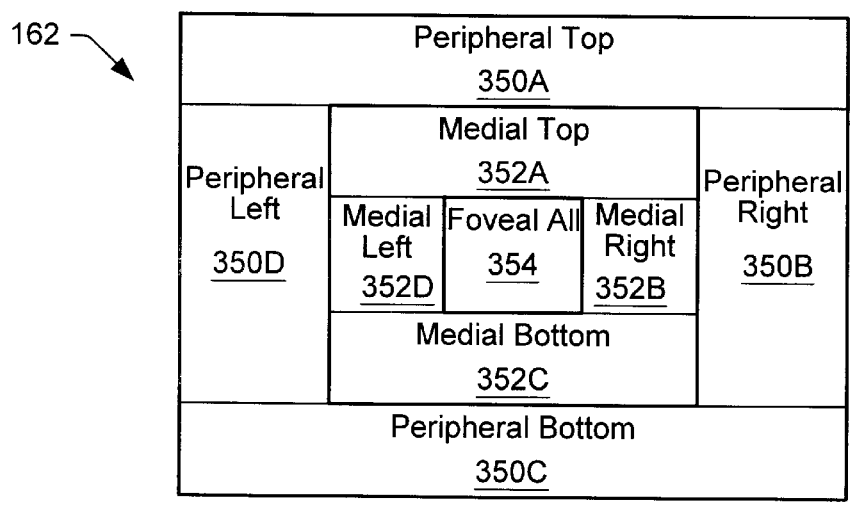
FIG. 16 is a diagram illustrating another embodiment of a method for dividing a super-sampled sample buffer into regions.

To simply perform calculations for polygons that encompass one or more region corners (e.g., a foveal region corner), the sample buffer may be further divided into a plurality of subregions. Turning now to FIG. 16, one embodiment of sample buffer 162 divided into sub-regions is shown. Each of these sub-regions are rectangular, allowing graphics system 112 to translate from a 2D address with a sub-region to a linear address in sample buffer 162. Thus, in some embodiments each sub-region has a memory base address, indicating where storage for the pixels within the sub-region starts. Each sub-region may also have a "stride" parameter associated with its width.

Figure 17:
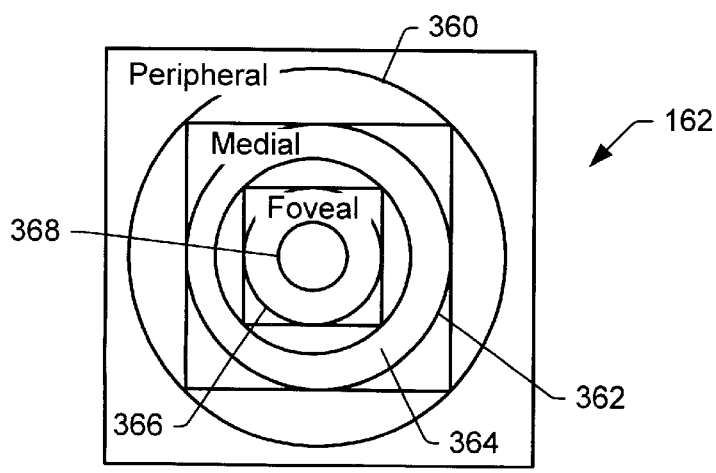
FIG. 17 is a diagram illustrating yet another embodiment of a method for dividing a super-sampled sample buffer into regions.

Another potential division of the super-sampled sample buffer is circular. Turning now to FIG. 17, one such embodiment is illustrated. For example, each region may have two radii associated with it (i.e., 360–368), dividing the region into three concentric circular-regions. The circular-regions may all be centered at the same screen point, the fovea center point. Note however, that the fovea center-point need not always be located at the center of the foveal region. In some instances it may even be located off-screen (i.e., to the side of the visual display surface of the display device). While the embodiment illustrated supports up to seven distinct circular-regions, it is possible for some of the circles to be shared across two different regions, thereby reducing the distinct circular-regions to five or less.

The circular regions may delineate areas of constant; sample density actually used. For example, in the example illustrated in the figure, foveal region 354 may allocate a sample buffer density of 8 samples per screen pixel, but outside the innermost circle 368, it may only use 4 samples per pixel, and outside the next circle 366 it may only use two samples per pixel. Thus, in this embodiment the rings need; not necessarily save actual memory (the regions do that), but they may potentially save memory bandwidth into and out of the sample buffer (as well as pixel convolution bandwidth). In addition to indicating a different effective sample density, the rings may also be used to indicate a different sample position scheme to be employed. As previously noted, these sample position schemes may stored in an on-chip RAM/ROM, or in programmable memory.

As previously discussed, in some embodiments super-sampled sample buffer 162 may be further divided into bins.

For example, a bin may store a single sample or an array of samples (e.g., 2×2 or 4×4 samples). In one embodiment, each bin may store between one and sixteen sample points, although other configurations are possible and contemplated. Each region may be configured with a particular bin size, and a constant memory sample density as well. Note that the lower density regions need not necessarily have larger bin sizes. In one embodiment, the regions (or at least the inner regions) are exact integer multiples of the bin size enclosing the region. This may allow for more efficient utilization of the sample buffer in some embodiments.

Variable-resolution super-sampling involves calculating a variable number of samples for each pixel displayed on the display device. Certain areas of an image may benefit from a greater number of samples (e.g., near object edges), while other areas may not need extra samples (e.g., smooth areas having a constant color and brightness). To save memory and bandwidth, extra samples may be used only in areas that may benefit from the increased resolution. For example, if part of the display is colored a constant color of blue (e.g., as in a background), then extra samples may not be particularly useful because they will all simply have the constant value (equal to the background color being displayed). In contrast, if a second area on the screen is displaying a 3D rendered object with complex textures and edges, the use of additional samples may be useful in avoiding certain artifacts such as aliasing. A number of different methods may be used to determine or predict which areas of an image would benefit from higher sample densities. For example, an edge analysis could be performed on the final image, and with that information being used to predict how the sample densities should be distributed. The software application may also be able to indicate which areas of a frame should be allocated higher sample densities.

A number of different method s may be used to implement variable-resolution super sampling. These methods tend to fall into the following two general categories: (1) those methods that concern the draw or rendering process, and (2) those methods that concern the convolution process. For example, samples may be rendered into the super-sampling sample buffer 162 using any of the following methods:

1) a uniform sample density;
2) varying sample density on a per-region basis (e.g., medial, foveal, and peripheral); and
3) varying sample density by changing density on a scan-line basis (or on a small number of scan lines basis).

Varying sample density on a scan-line basis may be accomplished by using a look-up table of densities. For example, the table may specify that the first five pixels of a particular scan line have three samples each, while the next four pixels have, two samples each, and so on.

On the convolution side, the following methods are possible:

1) a uniform convolution filter;
2) continuously variable convolution filter; and
3) a convolution filter operating at multiple spatial frequencies.

A uniform convolve filter may, for example, have a constant extent (or number of samples selected for each pixel calculated. In contrast, a continuously variable convolution filter may gradually change the number of samples used to calculate a pixel. The function may be vary continuously from a maximum at the center of attention to a minimum in peripheral areas.

Different combinations of these methods (both on the rendering side and convolution side) are also possible. For example, a constant sample density may be used on the rendering side, while a continuously variable convolution filter may be used on the samples.

Different methods for determining which areas of the image will be allocated more samples per pixel are also contemplated. In one embodiment, if the image on the screen has a main focal point (e.g., a character like Mario in a computer game), then more samples may be calculated for the area around Mario and fewer samples may be calculated for pixels in other areas (e.g., around the background or near the edges of the screen).

In another embodiment, the viewer's point of foveation may be determined by eye/head/hand-tracking. In head-tracking embodiments, the direction of the viewer's gaze is determined or estimated from the orientation of the viewer's head, which may be measured using a variety of mechanisms. For example, a helmet or visor worn by the viewer (with eye/head tracking) may be used alone or in combination with a hand-tracking mechanism, wand, or eye-tracking sensor to provide orientation information to graphics system 112. Other alternatives include head-tracking using an infrared reflective dot placed on the user's forehead, or using a pair of glasses with head- and or eye-tracking sensors built in. One method for using head- and hand-tracking is disclosed in U.S. Pat. No. 5,446,834 (entitled "Method and Apparatus for High Resolution Virtual Reality Systems Using Head Tracked Display," by Michael Deering, issued Aug. 29, 1995), which is incorporated herein by reference in its entirety. Other methods for head tracking are also possible and contemplated (e.g., infrared sensors, electromagnetic sensors, capacitive sensors, video cameras, sonic and ultrasonic detectors, clothing based sensors, video tracking devices, conductive ink, strain gauges, force-feedback detectors, fiber optic sensors, pneumatic sensors, magnetic tracking devices, and mechanical switches).

As previously noted, eye-tracking may be particularly advantageous when used in conjunction with head-tracking. In eye-tracked embodiments, the direction of the viewer's gaze is measured directly by detecting the orientation of the viewer's eyes in relation to the viewer's head. This information, when combined with other information regarding the position and orientation of the viewer's head in relation to the display device, may allow an accurate measurement of viewer's point of foveation (or points of foveation if two eye-tracking sensors are used). One possible method for eye tracking is disclosed in U.S. Pat. No. 5,638,176 (entitled "Inexpensive Interferometric Eye Tracking System"). Other methods for eye tracking are also possible and contemplated (e.g., the methods for head tracking listed above).

Regardless of which method is used, as the viewer's point of foveation changes position, so does the distribution of samples. For example, if the viewer's gaze is focused on the upper left-hand corner of the screen, the pixels corresponding to the upper left-hand corner of the screen may each be allocated eight or sixteen samples, while the pixels in the opposite corner (i.e., the lower right-hand corner of the screen) may be allocated only one or two samples per pixel. Once the viewer's gaze changes, so does the allotment of samples per pixel. When the viewer's gaze moves to the lower right-hand corner of the screen, the pixels in the upper left-hand corner of the screen may be allocated only one or two samples per pixel. Thus the number of samples per pixel may be actively changed for different regions of the screen in relation the viewer's point of foveation. Note in some embodiments, multiple users may be each have head/eye/hand tracking mechanisms that provide input to graphics system 112. In these embodiments, there may conceivably be two or more points of foveation on the screen, with corresponding areas of high and low sample densities. As previously noted, these sample densities may affect the render process only, the filter process only, or both processes.

Turning now to FIGS. 18A–B, one embodiment of a method for apportioning the number of samples per pixel is shown. The method apportions the number of samples based on the location of the pixel relative to one or more points of foveation. In FIG. 18A, an eye- or head-tracking device 360 is used to determine the point of foveation 362 (i.e., the focal point of a viewer's gaze). This may be determined by using tracking device 360 to determine the direction that the viewer's eyes (represented as 364 in the figure) are facing. As the figure illustrates, in this embodiment, the pixels are divided into foveal region 354 (which may be centered around the point of foveation 362), medial region 352, and peripheral region 350.

Three sample pixels are indicated in the figure. Sample pixel 374 is located within foveal region 314. Assuming foveal region 314 is configured with bins having eight samples, and assuming the convolution radius for each pixel touches four bins, then a maximum of 32 samples may contribute to each pixel. Sample pixel 372 is located within medial region 352. Assuming medial region 352 is configured with bins having four samples, and assuming the convolution radius for each pixel touches four bins, then a maximum of 16 samples may contribute to each pixel. Sample pixel 370 is located within peripheral region 350. Assuming peripheral region 370 is configured with bins having one sample each, and assuming the convolution radius for each pixel touches one bin, then there is a one sample to pixel correlation for pixels in peripheral region 350. Note these values are merely examples and a different number of regions, samples per bin, and convolution radius may be used.

Turning now to FIG. 18B, the same example is shown, but with a different point of foveation 362. As the figure illustrates, when tracking device 360 detects a change in the position of point of foveation 362, it provides input to the graphics system, which then adjusts the position of foveal region 354 and medial region 352. In some embodiments, parts of some of the regions (e.g., medial region 352) may extend beyond the edge of display device 84. In this example, pixel 370 is now within foveal region 354, while pixels 372 and 374 are now within the peripheral region. Assuming the sample configuration as the example in FIG. 18A, a maximum of 32 samples may contribute to pixel 370, while only one sample will contribute to pixels 372 and 374. Advantageously, this configuration may allocate more samples for regions that are near the point of foveation (i.e., the focal point of the viewer's gaze). This may provide a more realistic image to the viewer without the need to calculate a large number of samples for every pixel on display device 84.

Figure 19A:
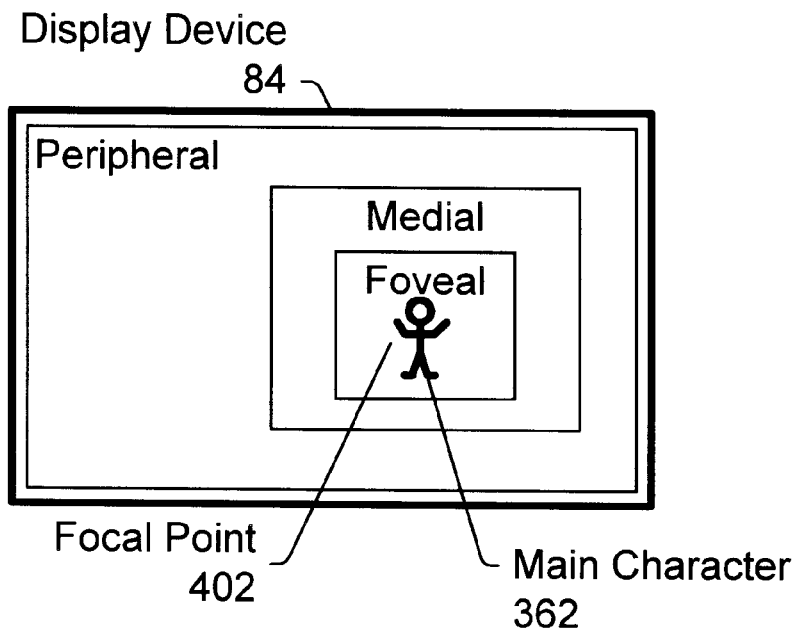
FIGS. 19A–B are diagrams illustrating one embodiment of a graphics system configured to vary region position according to the position of a cursor or visual object.
Figure 19B:
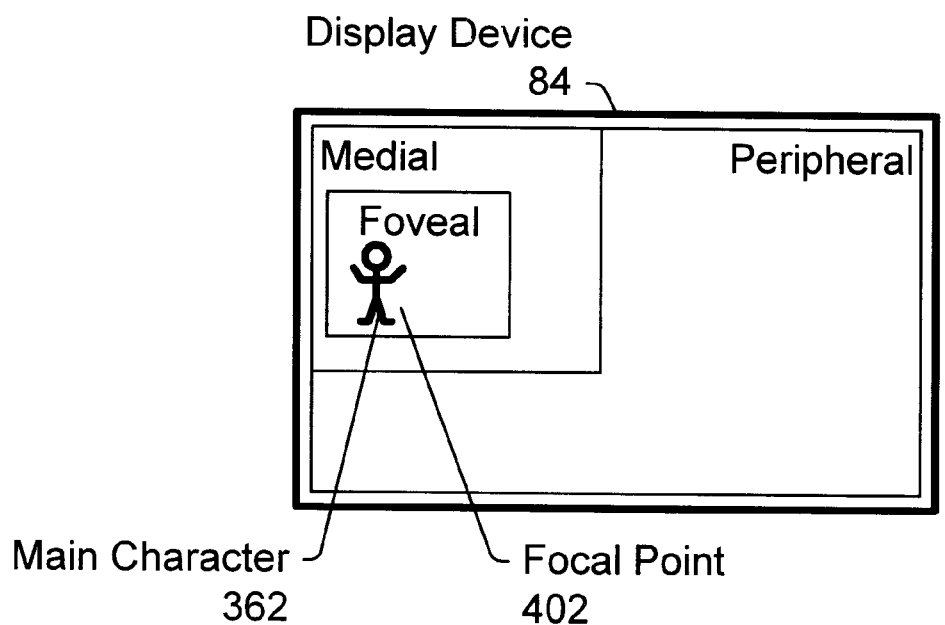

Turning now to FIGS. 19A–B, another embodiment of a computer system configured with a variable resolution super-sampled sample buffer is shown. In this embodiment, the center of the viewer's attention is determined, by position of a main character 362. Medial and foveal regions are centered around main character 362 as it moves around the screen. In some embodiments main character may be a simple cursor (e.g., as moved by keyboard input or by a mouse).

In still another embodiment, regions with higher sample density may be centered around the middle of display device 84's screen. Advantageously, this may require less control software and hardware while still providing a shaper image in the center of the screen (where the viewer's attention may be focused the majority of the time).

Computer Network—FIG. 20

Referring now to FIG. 20, a computer network 500 is shown comprising at least one server computer 502 and one or more client computers 506A–N. (In the embodiment shown in FIG. 4, client computers 506A–B are depicted). One or more of the client systems may be configured similarly to computer system 80, with each having one or more graphics systems 112 as described above. Server 502 and client(s) 506 may be joined through a variety of connections 504, such as a local-area network (LAN), a wide-area network (WAN), or an Internet connection. In one embodiment, server 502 may store and transmit 3-D geometry data (which may be compressed) to one or more of clients 506. The clients 506 receive the compressed 3-D geometry data, decompress it (if necessary) and then render the geometry data. The rendered image is then displayed on the client's display device. The clients render the geometry data and display the image using super-sampled sample buffer and real-time filter techniques described above. In another embodiment, the compressed 3-D geometry data may be transferred between client computers 506.

Additional Graphics System Features

Depending upon the implementation, computer system 80 may be configured to perform one or more of the following techniques in real-time using graphics system 112 (and super-sampled sample buffer 162): high-quality texture filtering, bump mapping, displacement mapping, multiple texture mapping, decompression of compressed graphics data, per-pixel Phong shading, depth of field effects, alpha buffering, soft-key output, 12-bit effective linear output, and integral eye-head-hand tracking. Each of these techniques will be described in detail further below.

A. Texture Filtering—FIGS. 21–22

Figure 21A:
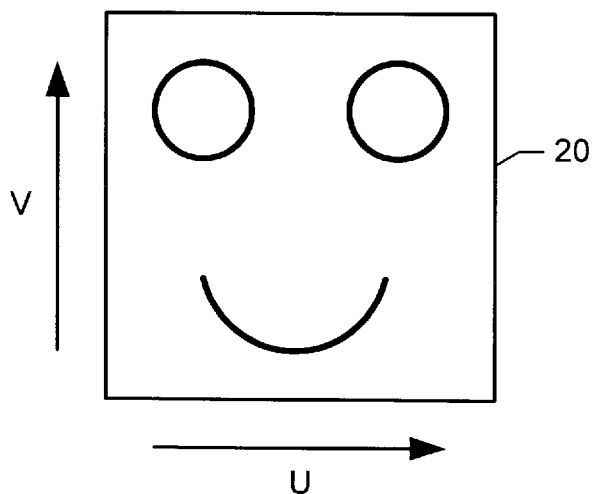
FIG. 21A illustrates an example of one embodiment of a texture map.
Figure 21B:
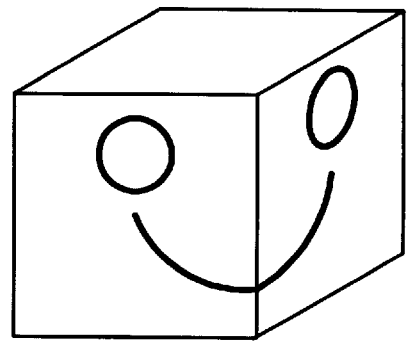
FIG. 21B illustrates an example of one embodiment of texture mapping onto a cube.
Figure 21C:
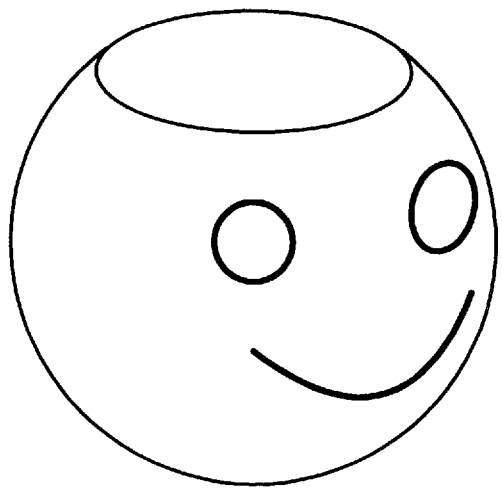
FIG. 21C illustrates an example of texture mapping onto a spherical object.

One popular technique to improve the realism of images displayed on a computer system is texture mapping. Texture mapping maps an image comprising a plurality of pixel values or texel values (called a "texture map") onto the surface of an object. A texture map is an image which can be wrapped (or mapped) onto a three-dimensional (3D) object. An example of a texture map 20 is illustrated in FIG. 21A. Texture map 20 is defined as a collection of texture elements 22a–n ("texels"), with coordinates U and V (similar to X and Y coordinates on the display or "screen space"). In FIG. 21B, an example of texture mapping is shown. As the figure illustrates, texture map 20 is mapped onto two sides of a three dimensional cube. FIG. 21C shows another example of texture mapping, but this time onto a spherical object. Another example would be to map an image of a painting with intricate details onto a series of polygons representing a vase.

While texture mapping may result in more realistic scenes, awkward side effects of texture mapping may occur unless the graphics subsystem can apply texture maps with correct perspective. Perspective-corrected texture mapping involves an algorithm that translates texels (i.e., pixels from the bitmap texture image) into display pixels in accordance with the spatial orientation of the surface.

In conjunction with texture mapping, many graphics subsystems utilize bilinear filtering, anti-aliasing, and mip mapping to further improve the appearance of rendered images. Bilinear filtering improves the appearance of texture mapped surfaces by considering the values of a number of adjacent texels (e.g., four) in order to determine the value of the displayed pixel. Bilinear filtering may reduce some of the "blockiness" that results from simple point sampling when adjacent display pixel values are defined by a single texel.

As previously described, aliasing refers to the jagged edges that result from displaying a smooth object on a computer display. Aliasing may be particularly disconcerting at the edges of texture maps. Anti-aliasing (i.e., minimizing the appearance of jagged edges) avoids this distraction by reducing the contrast between the edges where different sections of the texture map meet. This is typically accomplished by adjusting pixel values at or near the edge.

Mip-mapping involves storing multiple copies of texture maps, each digitized at a different resolution. When a texture-mapped polygon is smaller than the texture image itself, undesirable effects may result during texture mapping. Mip mapping avoids this problem by providing a large version of a texture map for use when the object is close to the viewer (i.e., large), and smaller versions of the texture map for use when the object shrinks from view.

A mip-map may be visualized as a pyramid of filtered versions of the same texture map. Each map has one-half the linear resolution of its preceding map, and has therefore one quarter the number of texels. The memory cost of this organization, where the coarsest level has only one texel, is $4/3$ (i.e., $1+\frac{1}{4}+\frac{1}{16}+\ldots$) the cost of the original map. The acronym "mip" stands for "multum in parvo" a Latin phrase meaning "many things in a small place". The mip-map scheme thus provides pre-filtered textures, one of which is selected at run time for use in rendering. In general, the desired level will not exactly match one of the predetermined levels in the mip-map. Thus, interpolation may be involved to calculate the desired level. Bilinear interpolation may be used if the texel to be looked up is not exactly on the integer boundaries of the predetermined mip-map levels. Similar two-dimensional linear interpolations are computed in each mip-map when scaled (u, v) values for texture table lookup are not integer values. To assure continuity when rapidly changing images (e.g., during animation), the effects of the four texels which enclose the scaled (u, v) values are considered, based upon their linear distances from the reference point in texel space. For example, if the scaled (u, v) values are (3.7, 6.8), the weighted average of texels (3, 6), (4, 6), (3, 7), and (4, 7) is taken.

Figure 22:
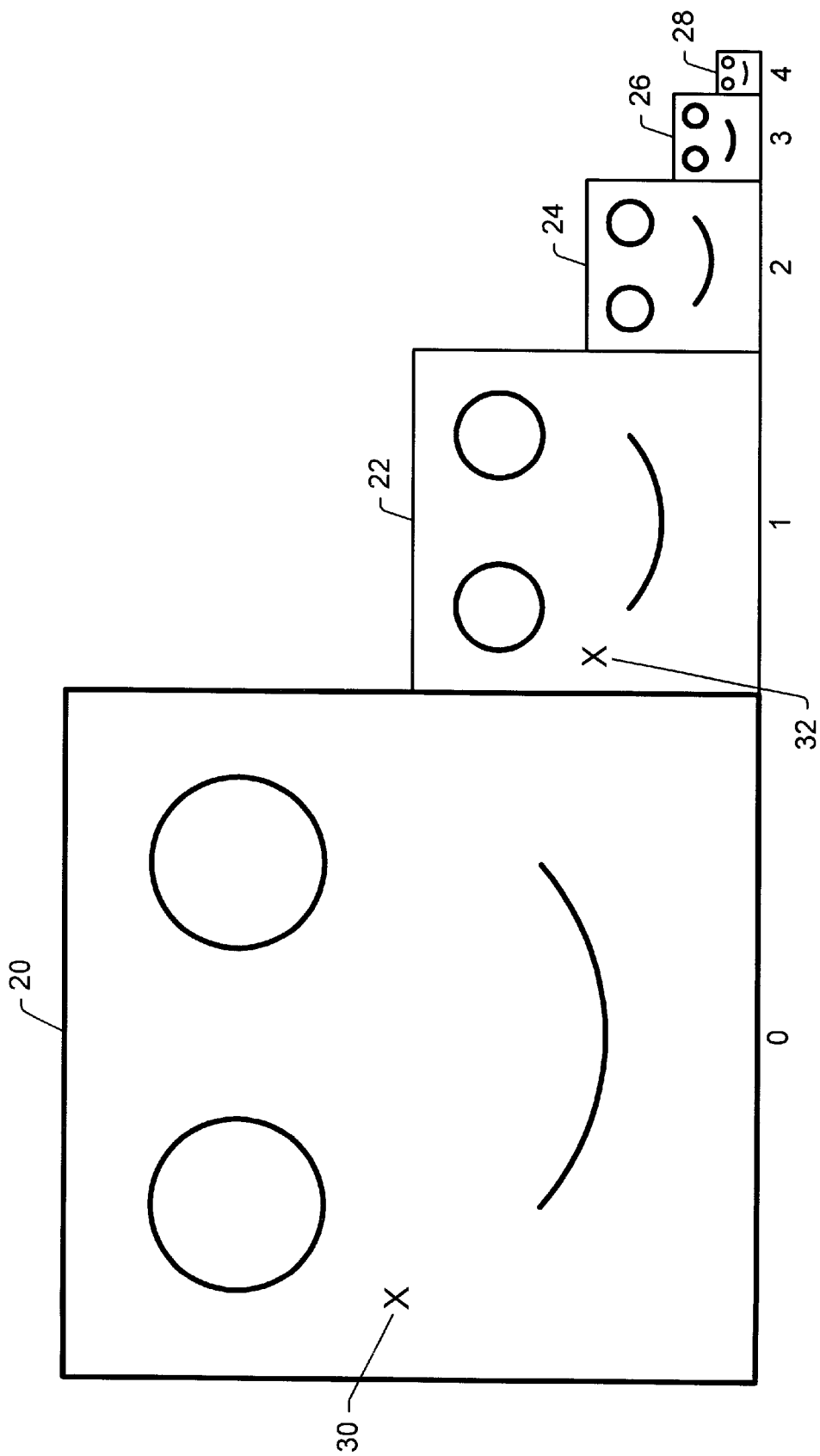
FIG. 22 illustrates an example of one embodiment of a mip-map.

Turning now to FIG. 22, a set of mip maps is shown. As the figure illustrates, each mip map is a two dimensional image, where each successive mip map is one half the size of the previous one. For example, if level 0 (i.e., texture map 20) is sixteen by sixteen texels, then level 1 (mip map 22) is eight by eight texels, level 2 (mip map 24) is four by four texels, level 3 (mip map 24) is two by two texels, and level 4 (mip map 28) is a single texel. Each subsequent mip map is one half the dimension of the previous mip map. Thus, each subsequent mip map has one quarter the area, number of texels, and resolution of the previous mip map. Note however, that other ratios are also possible and that mip maps need not be square.

Tri-linear filtering may be used to smooth out edges of mip mapped polygons and prevent moving objects from displaying a distracting 'sparkle' resulting from mismatched texture intersections. Trilinear filtering involves blending texels from two neighboring mip maps (e.g., blending texels from mip map 20 and mip map 22). The texel addresses in the neighboring mip maps are related by their addresses. For example, a particular texel at address (U,V) in level N corresponds to the texel at address (U/2, V/2) in level N+1. This is represented by texels 30 and 32 in the figure (each marked with an "x").

Current texture mapping hardware tends to implement simple bi- or tri-linear interpolation of mip-map textured images. Bi-linear filters, however, are effectively "tent" filters that are uniform in texture space, not screen space. Uniformity in screen space, however, tends to result in a more realistic image.

Currently, most high quality texture mapping is actually performed by software. While a variety of different techniques are used, most may be classified generally as "elliptical filters" (i.e., elliptical in texture space, but circular in screen space). These elliptical filters produce more realistic results, but are also considerably more complex than a tent filter. This complexity has prevented most real-time hardware implementations.

In one embodiment, graphics system 112 may be configured to perform real-time high quality texture mapping by converting texels into micro-polygons (e.g., triangles) at render time. These micro-polygons are then rendered into super-sampled sample buffer 162 using bi-linear interpolation. The final filtering (which produces the high quality image) is deferred until the convolution is performed. This allows all samples that might effect the final pixel value to be written into sample buffer 162 before the pixel value is calculated. The final filtering may then advantageously be performed in screen space. In one embodiment, one to two hundred samples may be filtered to generate a single pixel. This may significantly improve the appearance of the final image in some embodiments when compared with traditional hardware texture mapping systems that only filter four to eight texels to create a pixel.

In one embodiment, graphics system 112 may also be configured to perform one or more of the following advanced texturing techniques: bump mapping, displacement mapping, and multiple texture mapping.

B. Bump Mapping

Bump mapping perturbs the normal on a surface to create what appears to be small wrinkles or bumps on the surface. This technique breaks down near the silhouette of an object (because the silhouette of the object is in fact unchanged, the bumps implied by the shading are not visible in the geometry), and at near-glancing angles to the surface (because there is no blocking or geometric attenuation due to the bumps. In general, though, as long as the bumps are very small and the object is some distance away, bump mapping is an effective way to imply small deformations to a shape without actually changing the geometry.

C. Displacement Mapping

Displacement mapping actually moves the surface by a given amount in a given direction. Rendering displacement-mapped surfaces can present a challenge to some systems, particularly when the displacements become large. The results are often much better than with bump mapping, because displacement mapped objects may actually exhibit self-hiding and potentially shelf-shadowing features, as well as a changed silhouette.

D. Multiple Texture Mapping

Multiple texture mapping involves blending a number of different texture maps together to from the texture applied to the object. For example, a texture of fabric may be blended with a texture of marble so that it may appear that the fabric is semi-transparent and covering a marble object.

Another example of multiple texture mapping is taking a texture map of corresponding light and dark areas (i.e., a low-frequency shadow map), and then blending the shadow map with a texture (e.g., a high-frequency texture map). Multiple texture mapping may also be used for "micro-detail" applications. For example, when a viewer zooms in on a texture-mapped wall, the texture map for the wall may be blended with a low-resolution intensity map to provide more realistic imperfections and variations in the finish of the wall.

E. Decompression of Compressed Graphics Data

As previously noted, some embodiments of graphics system 112 may be configured to receive and decompress compressed 3D geometry data. This may advantageously reduce the memory bandwidth requirements within graphics system 112, as well as allow objects with a larger number of polygons to be rendered in real time.

F. Per-pixel Phong Shading

As previously noted, in some embodiments graphics system 112 may be configured to break textures into subpixel triangle fragments (see Texture Filtering above). By combining this feature with geometry compression (see Decompression of Compressed Graphics Data above) and an extremely high triangle render rate, graphics system 112 may, in some embodiments, be capable of achieving image quality rivaling, equaling, or even surpassing that of per-pixel Phong shading. These high quality images may be achieved by finely tessellating the objects to be rendered using micro-polygons. By finely tesselating the objects, a smoother and more accurate image is created without the need for per-pixel Phong shading. For example, hardware in graphics system may be configured to automatically turn all primitives into micro-triangles (i.e., triangles that are one pixel or less in size) before lighting and texturing is performed.

G. Soft-key Output

In some environments, users of graphics systems may desire the ability to output high quality anti-aliased rendered images that can be overlaid on top of a live video stream. While some systems exist that offer this capability, they are typically quite expensive. In one embodiment, graphics system 112 may be configured to inexpensively generate high quality overlays. In one embodiment, graphics system 112 may be configured to generate an accurate soft edge alpha key for video output and down stream alpha keying. The alpha key may be generated by sample-to-pixel calculation units 170, which may perform a filtering function on the alpha values stored in sample buffer 162 to form "alpha pixels." Each alpha pixel may correspond to a particular output pixel. In one embodiment, the alpha pixels may be output using DAC 178A while the color output pixels may be output by DAC 178B.

In another embodiment, this soft edge alpha key overlay is then output in a digital format to an external mixing unit which blends the overlay with a live video feed. The alpha pixels corresponding to each output pixel will determine how much of the live video shows through the corresponding pixel of the overlay. In one embodiment, for example, the greater the alpha pixel value, the more opaque the pixel becomes (and the less the live video feed shows through the pixel). Similarly, the smaller the alpha pixel value, the more transparent the pixel becomes. Other embodiments are also possible and contemplated. For example, the live video feed could be input into computer system 80 or graphics system 112. Graphics system 112 could then blend the two sources internally and output the combined video signal.

H. 12-bit Effective Linear Output

While 12-bit (linear light) color depth (i.e., 12-bits of data for each of red, green, and blue) is considered ideal in many embodiments, possible limitations in sample memories 162 may limit the storage space per sample to a lesser value (e.g., 10-bits per color component). In one embodiment, graphics system 112 may be configured to dither samples from 12-bits to 10-bits before they are stored in sample buffer 162. During the final anti-aliasing computation in sample-to-pixel calculation units 170A–D, the additional bits may effectively be recovered. After normalization, the resulting pixels may be accurate to 12-bits (linear light). The output pixels may be converted to nonlinear light, and after the translation, the results may be accurate to 10 bits (non-linear light). After conversion from linear to non-linear light, the resulting pixels may thus be accurate to 10-bits.

I. Integrated Eye-Head-Hand Tracking

As previously noted, some embodiments of graphics system 112 may be configured to support eye, head, and or hand tracking by modifying the number of samples per pixel at the viewer's point of foveation.

J. Alpha Blending, Fogging, and Depth-Cueing

Alpha blending is a technique that controls the transparency of an object, allowing realistic rendering of translucent surfaces such as glass or water. Additional atmospheric effects that are found in rendering engines include fogging and depth cueing. Both of these techniques obscure an object as it moves away from the viewer. Blur is also somewhat related and may be implemented by performing low-pass filtering during the filtering and sample-to-pixel calculation process (e.g., by using a larger extent during the filtering process) by sample-to-pixel calculation units 170A–D. An alpha value may be generated that can be used to blend the current sample into the sample buffer.

Although the embodiments above have been described in considerable detail, other versions are possible. Numerous variations and modifications will become apparent to those skilled in the art once the above disclosure is fully appreciated. It is intended that the following claims be interpreted to embrace all such variations and modifications. Note the headings used herein are for organizational purposes only and are not meant to limit the description provided herein or the claims attached hereto.

What is claimed is:

1. A graphics system comprising:
    a graphics processor configured receive 3D graphics data, wherein the graphics processor is configured to generate a plurality of samples from the 3D graphics data;
    a super-sampled sample buffer coupled to receive and store the samples from the graphics processor, wherein said super-sampled sample buffer is configured to double buffer at least a portion of each stored sample; and
    a sample-to-pixel calculation unit coupled to receive samples from the super-sampled sample buffer, wherein the sample-to-pixel calculation unit is configured to form output pixels in real time, wherein the sample-to-pixel calculation unit is configured to convey the output pixels to a display device without storing the output pixels in an intervening frame buffer.

2. The graphics system as recited in claim 1, wherein the sample-to-pixel calculation unit is configured to form each output pixel from the samples once per display device refresh cycle.

3. The graphics system as recited in claim 1, wherein the sample buffer is further configured to store alpha information for at least a portion of the samples stored therein.

4. The graphics system as recited in claim 1, wherein the sample-to-pixel calculation unit is programmable to change parameters governing the filtering performed by the sample-to-pixel calculation unit.

5. The graphics system as recited in claim 1, wherein the sample-to-pixel calculation unit is programmable to change parameters governing the filtering performed by the sample-to-pixel calculation unit on a frame-by-frame basis.

6. The graphics system as recited in claim 1, further comprising a second sample-to-pixel calculation unit, wherein the second sample-to-pixel calculation unit and the first sample-to-pixel calculation unit are configured to operate in parallel.

7. The graphics system as recited in claim 1, further comprising a second sample-to-pixel calculation unit, wherein each sample-to-pixel calculation unit is configured to receive samples corresponding to a particular region of the sample buffer.

8. The graphics system as recited in claim 7, wherein the particular regions overlap.

9. The graphics system as recited in claim 1, wherein the samples are stored in the sample buffer in bins.

10. The graphics system as recited in claim 9, wherein each bin defines the approximate position of each sample within the bin, wherein the precise position of each sample within the bin is determined by adding x-offsets and y-offsets associated with the sample to the sample's bin position.

11. The graphics system as recited in claim 10, wherein each sample's x-offset and y-offset are stored in the sample buffer.

12. The graphics system as recited in claim 11, further comprising a sample position memory coupled to the sample-to-pixel calculation unit, wherein each sample's x-offset and y-offset are stored in the sample position memory.

13. The graphics system as recited in claim 1, wherein the sample-to-pixel calculation unit is configured to determine a particular output pixel's color values by:
  multiplying each sample that falls within a predetermined region around the particular output pixel's center by a weighting factor; and
  summing the weighted samples.

14. A method for operating a graphics system comprising:
  receiving 3D graphics data, wherein the 3D graphics data comprises a plurality of graphics primitives;
  calculating a plurality of sample positions;
  determining which sample positions are within the graphics primitives;
  rendering the samples that are within the graphics primitives;
  storing the rendered samples in sample buffer, wherein at least a portion of each stored sample is double-buffered;
  filtering the stored samples once per screen refresh cycle to generate an output pixel; and
  providing the output pixel to a display device without buffering the output pixel in a frame buffer after said filtering.

15. The method as recited in claim 14, wherein the filtering comprises:
  reading a group of samples from the sample buffer;
  determining which samples within the group are located within a predetermined extent from the center of the output pixel being generated;
  applying a scaling factor to each sample within the predetermined distance;
  summing the scaled samples to form the output pixel; and
  normalizing the output pixel.

16. The method as recited in claim 14, wherein the filtering comprises:
  reading a group of samples from the sample buffer;
  determining which samples within the group are located within a predetermined distance from the center of the output pixel being generated;
  applying a scaling factor to each sample within the predetermined distance;
  summing the scaled samples to form the output pixel; and
  normalizing the output pixel.

17. The method as recited in claim 16, wherein the scaling factor varies as a function of the sample's distance from the center of the output pixel.

18. The method as recited in claim 16, wherein the scaling factor varies as a function of the sample's x-offset and y-offset from the center of the output pixel.

19. The method as recited in claim 14, further comprising storing an alpha value for at least a portion of the samples stored in the sample buffer.

20. The method as recited in claim 14, wherein the filtering comprises mathematically manipulating samples located within a predetermined distance from the center of the output pixel.

21. The method as recited in claim 14, wherein the filter used in the filtering is changeable at least as frequently as the screen refresh cycle.

22. The method as recited in claim 14, wherein the storing comprises storing the samples in bins, where each sample's position is determined by adding an x-offset and a y-offset to the corresponding bin's position.

23. The method as recited in claim 22, wherein the filtering comprises reading at least part of one or more columns of bins from the sample buffer, wherein the columns overlap.

24. The method as recited in claim 14, wherein said sample buffer is divided into multiple columns that are filtered in parallel.

25. The method as recited in claim 14, further comprising storing x-offsets and y-offsets for each sample stored in the sample buffer.

26. The method as recited in claim 25, wherein the filter is changeable at least as frequently as the screen refresh cycle.

27. The method as recited in claim 14, wherein the number of samples contributing to each output pixel varies.

28. A computer system configured to display 3D graphics images, the system comprising:
  a microprocessor,
  a main memory:
  a bus coupling the microprocessor and the main memory; and
  a graphics system coupled to the main memory, wherein the graphics system comprises:
    a graphics processor configured receive 3D graphics data, wherein the 3D graphics data comprises a plurality of graphics primitives,
    a sample buffer coupled to receive and store the samples from the graphics processor, wherein said sample buffer is configured to double buffer at least a portion of each stored sample, and
    a sample-to-pixel calculation unit coupled to receive samples from the sample buffer, wherein the sample-to-pixel calculation unit is configured to form output pixels, wherein the sample-to-pixel calculation unit is configured to convey the output pixels to a display device without buffering frames of the output pixels, wherein said sample-to-pixel calculation unit is configured to form each output pixel once per frame.

29. The computer system as recited in claim 28, wherein the sample buffer is further configured to store alpha information for at least a portion of the samples stored therein.

30. A computer software program embodied on computer readable media, wherein the software program comprises a plurality of instructions configured to direct a graphics processor to:

generate a plurality of sample positions;

calculate a sample for the sample positions;

store the sample in a sample buffer, wherein at least a part of each sample is double buffered;

read one or more of the samples from the sample buffer;

filter one or more of the stored samples once per screen refresh cycle to form output pixels in real time; and convey the output pixels to a display device without storing the output pixel in a frame buffer after said filtering.

31. The computer software program as recited in claim 30, wherein the plurality of instructions are further configured to modify the filter used.

32. The computer software program as recited in claim 30, wherein more than one sample contributes to each output pixel.

33. The computer software program as recited in claim 30, wherein the output pixels are conveyed to a display device without being stored in the sample buffer.

34. A graphics system comprising:

a graphics processor configured receive 3D graphics data, wherein the graphics processor is configured to generate a plurality of samples from the 3D graphics data;

a sample buffer coupled to receive and store the samples from the graphics processor; and a sample-to-pixel calculation unit coupled to receive samples from the sample buffer, wherein the sample-to-pixel calculation unit is configured to form output pixels that are directly conveyed to a display device.

35. The graphics system as recited in claim 34, wherein said output pixels are conveyed to the display device without being stored in a frame buffer.

36. The graphics system as recited in claim 34, wherein said sample-to-pixel calculation unit is configured to from said output pixels in real time.

37. A graphics system comprising:

a graphics processor configured receive 3D graphics data, wherein the graphics processor is configured to generate a plurality of samples from the 3D graphics data;

a super-sampled sample buffer coupled to receive and store the samples from the graphics processor, wherein said super-sampled sample buffer is configured to double buffer at least a portion of each stored sample; and a sample-to-pixel calculation unit coupled to receive samples from the super-sampled sample buffer, wherein the sample-to-pixel calculation unit is configured to form output pixels by filtering the samples in real time, wherein the sample-to-pixel calculation unit is configured to convey the output pixels to a display device without a frame buffer intervening between the sample-to-pixel calculation unit and the display device;

wherein the sample-to-pixel calculation unit is programmable to change parameters governing the filtering performed by the sample-to-pixel calculation unit.

38. The graphics system as recited in claim 37, wherein the sample-to-pixel calculation unit is configured to form each output pixel from the samples once per display device refresh cycle.

39. The graphics system as recited in claim 37, wherein the sample buffer is further configured to store alpha information for at least a portion of the samples stored therein.

40. The graphics system as recited in claim 37, wherein the sample-to-pixel calculation unit is programmable to change parameters governing the filtering performed by the sample-to-pixel calculation unit on a frame-by-frame basis.

41. The graphics system as recited in claim 37, further comprising a second sample-to-pixel calculation unit, wherein the second sample-to-pixel calculation unit and the first sample-to-pixel calculation unit are configured to operate in parallel.

42. The graphics system as recited in claim 37, further comprising a second sample-to-pixel calculation unit, wherein each sample-to-pixel calculation unit is configured to receive samples corresponding to a particular region of the sample buffer.

43. The graphics system as recited in claim 42, wherein the particular regions overlap.

44. The graphics system as recited in claim 37, wherein the samples are stored in the sample buffer in bins.

45. The graphics system as recited in claim 44, wherein each bin defines the approximate position of each sample within the bin, wherein the precise position of each sample within the bin is determined by adding x-offsets and y-offsets associated with the sample to the sample's bin position.

46. The graphics system as recited in claim 45, wherein each sample's x-offset and y-offset are stored in the sample buffer.

47. The graphics system as recited in claim 46, further comprising a sample position memory coupled to the sample-to-pixel calculation unit, wherein each sample's x-offset and y-offset are stored in the sample position memory.

48. The graphics system as recited in claim 37, wherein the sample-to-pixel calculation unit is configured to determine a particular output pixel's color values by:

multiplying each sample that falls within a predetermined region around the particular output pixel's center by a weighting factor; and summing the weighted samples.

49. A method for operating a graphics system comprising:

receiving 3D graphics data, wherein the 3D graphics data comprises a plurality of graphics primitives;

calculating a plurality of sample positions;

determining which sample positions are within the graphics primitives;

rendering the samples that are within the graphics primitives;

storing the rendered samples in sample buffer, wherein at least a portion of each stored sample is double-buffered; and filtering the stored samples once per screen refresh cycle to generate an output pixel;

providing the output pixel to a display device without buffering the output pixel in a frame buffer after said filtering;

wherein a filter used in said filtering is changeable at least as frequently as the screen refresh cycle.

50. The method as recited in claim 49, wherein the filtering comprises:

reading a group of samples from the sample buffer;

determining which samples within the group are located within a predetermined extent from the center of the output pixel being generated;

applying a scaling factor to each sample within the predetermined distance;

summing the scaled samples to form the output pixel; and normalizing the output pixel.

51. The method as recited in claim 49, wherein the filtering comprises:

reading a group of samples from the sample buffer;

determining which samples within the group are located within a predetermined distance from the center of the output pixel being generated;

applying a scaling factor to each sample within the predetermined distance;

summing the scaled samples to form the output pixel; and normalizing the output pixel.

52. The method as recited in claim 51, wherein the scaling factor varies as a function of the sample's distance from the center of the output pixel.

53. The method as recited in claim 51, wherein the scaling factor varies as a function of the sample's x-offset and y-offset from the center of the output pixel.

54. The method as recited in claim 49, further comprising storing an alpha value for at least a portion of the samples stored in the sample buffer.

55. The method as recited in claim 49, wherein the filtering comprises mathematically manipulating samples located within a predetermined distance from the center of the output pixel.

56. The method as recited in claim 49, wherein the storing comprises storing the samples in bins, where each sample's position is determined by adding an x-offset and a y-offset to the corresponding bin's position.

57. The method as recited in claim 56, wherein the filtering comprises reading at least part of one or more columns of bins from the sample buffer, wherein the columns overlap.

58. The method as recited in claim 49, wherein said sample buffer is divided into multiple columns that are filtered in parallel.

59. The method as recited in claim 49, further comprising storing x-offsets and y-offsets for each sample stored in the sample buffer.

60. The method as recited in claim 59, wherein the filter is changeable at least as frequently as the screen refresh cycle.

61. The method as recited in claim 49, wherein the number of samples contributing to each output pixel varies.

62. A computer system configured to display 3D graphics images, the system comprising:

a microprocessor;

a main memory;

a bus coupling the microprocessor and the main memory; and a graphics system coupled to the main memory, wherein the graphics system comprises:

a graphics processor configured receive 3D graphics data, wherein the 3D graphics data comprises a plurality of graphics primitives, a sample buffer coupled to receive and store the samples from the graphics processor, wherein said sample buffer is configured to double buffer at least a portion of each stored sample, and a sample-to-pixel calculation unit coupled to receive samples from the sample buffer, wherein the sample-to-pixel calculation unit is configured to form output pixels by filtering the samples, wherein the sample-to-pixel calculation unit is configured to convey the output pixels to a display device without storing the output pixels in a traditional frame buffer, wherein said sample-to-pixel calculation unit is configured to form each output pixel once per frame;

wherein the sample-to-pixel calculation unit is programmable to change parameters governing the filtering performed by the sample-to-pixel calculation unit.

63. The computer system as recited in claim 62, wherein the sample buffer is further configured to store alpha information for at least a portion of the samples stored therein.

64. A computer software program embodied on computer readable media, wherein the software program comprises a plurality of instructions configured to direct a graphics processor to:

generate a plurality of sample positions;

calculate samples at the sample positions;

store the samples in a sample buffer, wherein the samples are stored in the sample buffer in a double-buffered fashion;

read one or more of the samples from the sample buffer, filter one or more of the stored samples once per screen refresh cycle to form output pixels in real time; and convey the output pixels to a display device without buffering frames of the output pixels after said filtering;

wherein the plurality of instructions are further configured to modify a filter used to perform said filtering.

65. The computer software program as recited in claim 64, wherein more than one sample contributes to each output pixel.

66. The computer software program as recited in claim 64, wherein the output pixels are conveyed to a display device without being stored in the sample buffer.

67. A graphics system comprising:

a graphics processor configured receive 3D graphics data, wherein the graphics processor is configured to generate a plurality of samples from the 3D graphics data;

a sample buffer coupled to receive and store the samples from the graphics processor; and a sample-to-pixel calculation unit coupled to receive samples from the sample buffer, wherein the sample-to-pixel calculation unit is configured to filter the samples to generate output pixels that are directly conveyed to a display device, wherein the sample-to-pixel calculation unit is programmable to change parameters governing the filtering of said samples.

68. The graphics system as recited in claim 67, wherein said output pixels are conveyed to the display device without being stored in a frame buffer.

69. The graphics system as recited in claim 67, wherein said sample-to-pixel calculation unit is configured to from said output pixels in real time.

70. A graphics system comprising:

a graphics processor configured receive 3D graphics data, wherein the graphics processor is configured to generate a plurality of samples from the 3D graphics data;

a super-sampled sample buffer coupled to receive and store the samples from the graphics processor; and a sample-to-pixel calculation unit coupled to receive samples from the super-sampled sample buffer, wherein the sample-to-pixel calculation unit is configured to form output pixels in real time, wherein the sample-to-pixel calculation unit is configured to convey the output pixels to a display device without buffering the output pixels in a frame buffer.

71. The graphics system as recited in claim 70, wherein the sample-to-pixel calculation unit is configured to form each output pixel from the samples once per display device refresh cycle.

72. The graphics system as recited in claim 70, wherein the sample-to-pixel calculation unit is programmable to change parameters governing the filtering performed by the sample-to-pixel calculation unit.

73. A method for operating a graphics system comprising:
- receiving 3D graphics data, wherein the 3D graphics data comprises a plurality of graphics primitives;
- calculating a plurality of sample positions;
- determining which sample positions are within the graphics primitives;
- rendering the samples that are within the graphics primitives;
- storing the rendered samples in sample buffer;
- filtering the stored samples once per screen refresh cycle to generate an output pixel; and
- providing the output pixel to a display device without buffering the output pixel in a frame buffer after said filtering.

74. A computer system configured to display 3D graphics images, the system comprising:
- a microprocessor;
- a main memory;
- a bus coupling the microprocessor and the main memory; and
- a graphics system coupled to the main memory, wherein the graphics system comprises:
  - a graphics processor configured receive 3D graphics data, wherein the 3D graphics data comprises a plurality of graphics primitives,
  - a sample buffer coupled to receive and store the samples from the graphics processor; and
  - a sample-to-pixel calculation unit coupled to receive samples from the sample buffer, wherein the sample-to-pixel calculation unit is configured to form output pixels, wherein the sample-to-pixel calculation unit is configured to convey the output pixels to a display device without buffering the output pixels in a frame buffer, wherein said sample-to-pixel calculation unit is configured to form each output pixel once per frame.

* * * * *